United States Patent
Echavarren et al.

(10) Patent No.: US 10,604,469 B2
(45) Date of Patent: Mar. 31, 2020

(54) METHOD FOR THE PREPARATION OF A PARTIALLY HYDROGENATED POLYACENE AND AN INTERMEDIATE THEREOF

(71) Applicants: Fundacio Institut Catala D'Investigacio Quimica, Tarragona (ES); Universitat Rovira I Virgili, Tarragona (ES)

(72) Inventors: Antonio M. Echavarren, Tarragona (ES); Ruth Dorel, Tarragona (ES); Paul McGonigal, Pity Me Durham (GB)

(73) Assignees: Fundacio Institut Catala D'Investigacio Quimica, Tarragona (ES); Universitat Rovira I Virgili, Tarragona (ES)

( * ) Notice: Subject to any disclaimer, the term of this patent is extended or adjusted under 35 U.S.C. 154(b) by 0 days.

(21) Appl. No.: 16/320,691

(22) PCT Filed: Jan. 13, 2017

(86) PCT No.: PCT/EP2017/050676
§ 371 (c)(1),
(2) Date: Jan. 25, 2019

(87) PCT Pub. No.: WO2018/019436
PCT Pub. Date: Feb. 1, 2018

(65) Prior Publication Data
US 2019/0161426 A1  May 30, 2019

(30) Foreign Application Priority Data

Jul. 26, 2016 (EP) ..................................... 16382362

(51) Int. Cl.
| | |
|---|---|
| C07C 43/166 | (2006.01) |
| C07D 333/16 | (2006.01) |
| C07D 333/56 | (2006.01) |
| C07F 7/08 | (2006.01) |
| C07C 41/18 | (2006.01) |
| C07C 25/22 | (2006.01) |
| C07C 47/546 | (2006.01) |
| C07C 49/84 | (2006.01) |
| C07C 43/215 | (2006.01) |
| C07C 43/176 | (2006.01) |
| C07C 17/361 | (2006.01) |
| C07C 45/68 | (2006.01) |
| C07C 41/30 | (2006.01) |
| C07C 45/64 | (2006.01) |
| C07C 45/65 | (2006.01) |
| C07C 47/575 | (2006.01) |
| C07C 43/21 | (2006.01) |
| C07C 13/66 | (2006.01) |
| C07C 1/20 | (2006.01) |
| C07C 49/792 | (2006.01) |
| C07C 13/62 | (2006.01) |
| C07D 333/50 | (2006.01) |
| C07C 15/38 | (2006.01) |

(52) U.S. Cl.
CPC .............. *C07C 43/166* (2013.01); *C07C 1/20* (2013.01); *C07C 13/62* (2013.01); *C07C 13/66* (2013.01); *C07C 15/38* (2013.01); *C07C 17/361* (2013.01); *C07C 25/22* (2013.01); *C07C 41/18* (2013.01); *C07C 41/30* (2013.01); *C07C 43/176* (2013.01); *C07C 43/21* (2013.01); *C07C 43/215* (2013.01); *C07C 45/64* (2013.01); *C07C 45/65* (2013.01); *C07C 45/68* (2013.01); *C07C 47/546* (2013.01); *C07C 47/575* (2013.01); *C07C 49/792* (2013.01); *C07C 49/84* (2013.01); *C07D 333/16* (2013.01); *C07D 333/50* (2013.01); *C07D 333/56* (2013.01); *C07F 7/081* (2013.01); *C07C 2603/44* (2017.05); *C07C 2603/52* (2017.05); *C07C 2603/54* (2017.05)

(58) Field of Classification Search
None
See application file for complete search history.

(56) References Cited

PUBLICATIONS

PCT/EP2017/050676 International Search Report dated Apr. 20, 2017.
Jimenez-Nunez et al. "Evolution of Propargyl Ethers into Allylgold Cations in the Cyclization of Enynes," Angewandte Chemie International Edition, Aug. 3, 2009, 48(33):6152-6155.
Luo et al. "Linear Acene Derivatives. New Routes to Pentacene and Naphthacene and the First Synthesis of a Triptycene with Two Anthracene Moieties," The Journal of Organic Chemistry, 1987, 52(22):4833-4836.
Meiss et al. "Divergent Gold(I)—Catalyzed Skeletal Rearrangements of 1,7-Enynes," Chemistry—A European Journal, 2015, 21(39):13526-13530.

*Primary Examiner* — Ana Z Muresan
(74) *Attorney, Agent, or Firm* — Wagenknecht IP Law Group PC

(57) ABSTRACT

The present invention relates to a process for preparing a partially hydrogenated polyacene, and a novel intermediate used in such process; also the present invention relates to a process for preparing the corresponding conjugated polyacenes.

18 Claims, No Drawings

METHOD FOR THE PREPARATION OF A PARTIALLY HYDROGENATED POLYACENE AND AN INTERMEDIATE THEREOF

CROSS REFERENCE TO RELATED APPLICATIONS

This application is a US national phase under 35 USC § 371 of International Patent Application No. PCT/EP2017/050676, filed Jan. 13, 2017, which claims priority to European Patent Application No. 16382362.8, filed Jul. 26, 2016. Each of the applications referred to in this paragraph is herein incorporated by reference in their entireties.

The present invention relates to a process for preparing a partially hydrogenated polyacene, and a novel intermediate used in such process. Also, the present invention relates to a process for preparing the corresponding conjugated polyacenes. This invention is the result of a project which has received funding from the European Union's Horizon 2020 research and innovation program under grant agreement 837225-PLAT_ACE.

BACKGROUND ART

Large acenes find a growing number of applications in organic electronics. However their applicability is limited by their poor solubility and their inherent instability. One strategy widely exploited in order to overcome these limitations is the inclusion of appropriate substituents that increase both stability and solubility of acene derivatives. Another less explored way of "protecting" acenes consists of the preparation of partially hydrogenated analogues, which has been carried out by partial hydrogenation of polycyclic aromatic hydrocarbons or by reduction of the corresponding quinones.

There are different ways to obtain the partially hydrogenated polyacenes.

In the document titled Linear Acene Derivatives. New routes to pentacene and naphthacene and the first synthesis of a triptycene with two anthracene moieties, Jihmei Luo and Harold Hart, the Journal of organic chemistry, vol. 52, no 22, Oct. 30, 1987, 4833-4836; is described the synthesis of 5,14-dihydropentacene. Benzocyclobutene was heated with anthracene 1,4-endoxine in toluene and after a dehydration step with an acid the 5,14 dihydropentacene is obtained.

In the document titled *Fullerene-Acene Chemistry: diastereoselective synthesis of a cis,cis-tris[60]fullerene adduct of 6,8,15,17-tetraphenylheptacene*, Glen P. Miller and Jonanthan Briggs, *Organic letters*, 2003, vol. 5 no 22, 4203-4206 is described the synthesis of 5,7,9,14,16,18-hexahydro-6,8,15,17-tetraphenylheptacene. The 1,3-diphenylnaphthol[2,3-c]-furan reacts with p-benzoquinone, then a double dehydration with p-toluene sulfonic acid in benzene affords 6,8,15,17-tetraphenylheptacene-7,16-quinone, the reduction of this compound with hydriodic acid in acetic acid gives the 5,7,9,14,16,18-hexahydro-6,8,15,17-tetraphenylheptacene.

In the document titled *Divergent gold (I) catalyzed skeletal rearrangements of 1,7 enynes*, Rebecca Meiβ, Kamal Kumar and Herbert Waldmann *Chem. Eur. J.* 2015, 21, 13526-13530 is described the divergent skeletal rearrangement of 1,7-enynes into exocyclic allenes and tricyclic hexahydroanthracenes by catalysis with a cationic gold(I) complex. In this document are obtained tricyclic substituted hexahydroanthracenes, not dihydrotetracenes. The reaction only occurs with aromatic derivatives having at least two alkoxy substituents. Also the conditions of the process are extreme and low yields are reported.

Thus, from what is known in the art, it is derived that the development of a process for the production of partially hydrogenated polyacenes and the corresponding polyacenes that show high yield is still of great interest.

SUMMARY OF THE INVENTION

Inventors have found that 1,7 enynes are converted in the presence of a gold (I) catalyst into partially hydrogenated polyacenes. The process is advantageous since it results in an increase in the efficiency of the results and the hydrogenated polyacene obtained is a stable precursor of the corresponding conjugated polyacene.

Nothing in the art suggests the present invention.

Therefore the first aspect of the invention is a method for the preparation of a partially hydrogenated polyacene comprising the step of:
(i) contacting a compound of formula (I)

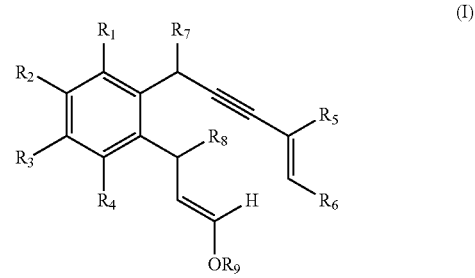

with a catalytically effective amount of a Au(I) catalyst, wherein each of $R_1$, $R_2$, $R_3$ and $R_4$, which may be the same or different, is independently selected from the group consisting of: hydrogen, halogen, straight chain or branched $(C_1-C_6)$alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)$alkyl$)_3$, $(C_2-C_6)$alkylcarbonylamino, $(C_2-C_6)$alkylaminocarbonyl, an aldehyde group, cyano, nitro, a radical of formula (II):

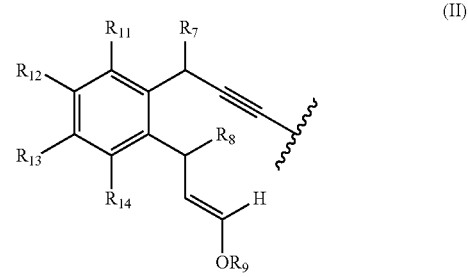

with the condition that when one or more of $R_1$, $R_2$, $R_3$ and $R_4$ is a radical of formula (II) at least one carbon atom adjacent to the carbon atom bearing a radical of formula (II) is substituted with hydrogen; a $(C_6-C_{20})$aryl optionally substituted at one or more positions with a radical selected from the group consisting of: halogen, $(C_1-C_6)$alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)$alkyl$)_3$, $(C_2-C_6)$ alkylcarbonylamino, $(C_2-C_6)$alkylaminocarbonyl, cyano, nitro, an aldehyde group and a radical of formula (II) with the condition that at least one carbon atom adjacent to the carbon atom of the $(C_6-C_{20})$aryl substituted with the radical of formula (II) is substituted with hydrogen; and a $(C_5-C_{20})$ heteroaryl optionally substituted at one or more positions with a radical selected from the group consisting of halogen, $(C_1-C_6)$alkyl, $(C_1-C_6)$haloalkyl, $(C_1-C_6)$alkyloxy, $(C_1-C_6)$ thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)$alkyl$)_3$, $(C_2-C_6)$alkylcarbonylamino, $(C_2-C_6)$alkylaminocarbonyl, cyano, nitro, an aldehyde group and a radical of formula (II) with the condition that at least one carbon atom adjacent to the carbon atom of the $(C_5-C_{20})$heteroaryl substituted with the radical of formula (II) is substituted with hydrogen; or, alternatively, one, two or three of the pairs $R_1$ and $R_2$, $R_2$ and $R_3$, and $R_3$ and $R_4$, together with the carbon atoms to which they are attached, form a ring system comprising 1 to 5 rings, each ring being isolated, fused or partially fused, and comprising from 5 to 6 members selected from the group consisting of: C, CH, $CH_2$, CO, O, S, N and $NR_{10}$, wherein $R_{10}$ is selected from hydrogen and $(C_1-C_6)$alkyl, each ring being independently unsaturated, saturated or aromatic; and each ring being further optionally substituted with one or more radicals selected from the group consisting of: halogen, $(C_1-C_6)$ alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$ alkyloxycarbonyl, a radical of formula $Si((C_1-C_6)$alkyl$)_3$, $(C_2-C_6)$alkylcarbonylamino, $(C_2-C_6)$alkylaminocarbonyl, cyano, an aldehyde group and nitro and wherein when the ring system comprises at least one carbon-carbon double bond, the carbon atoms forming a double bond can further be substituted with a radical of formula (II) with the condition that the carbon atom forming the double bond adjacent to the carbon atom substituted with a radical of formula (II) is substituted with hydrogen;

$R_7$ is selected from the group consisting of hydrogen, $(C_1-C_6)$alkyl and $(C_1-C_6)$haloalkyl; $R_8$ is selected from the group consisting of hydrogen, $(C_1-C_6)$alkyl, and $(C_1-C_6)$ haloalkyl; $R_9$ is a linear or branched $(C_1-C_6)$alkyl; and $R_{11}$, $R_{12}$, $R_{13}$, $R_{14}$ have the same meanings as $R_1$, $R_2$, $R_3$, $R_4$;

$R_5$ and $R_6$ are each independently selected from the group consisting of: hydrogen, straight chain or branched $(C_1-C_6)$ alkyl, $(C_1-C_6)$haloalkyl, a $(C_6-C_{20})$aryl optionally substituted at one or more positions with a radical selected from the group of halogen, $(C_1-C_6)$alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)$alkyl$)_3$, $(C_2-C_6)$alkylcarbonylamino, $(C_2-C_6)$alkylaminocarbonyl, cyano, nitro, an aldehyde group, and a radical of formula (II) with the condition that at least one carbon atom adjacent to the carbon atom of the $(C_6-C_{20})$aryl substituted with the radical of formula (II) is substituted with hydrogen; and a $(C_5-C_{20})$ heteroaryl optionally substituted at one or more positions with a radical selected from the group consisting of: halogen, $(C_1-C_6)$alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)$alkyl$)_3$, $(C_2-C_6)$alkylcarbonylamino, $(C_2-C_6)$ alkylaminocarbonyl, cyano, nitro, an aldehyde group, and a radical of formula (II) with the condition that at least one carbon atom adjacent to the carbon atom of the $(C_5-C_{20})$ heteroaryl substituted with the radical of formula (II) is substituted with hydrogen; or, alternatively, $R_5$ and $R_6$, together with the carbon atoms to which they are attached, form a ring system comprising 1 to 10 rings, each ring being isolated, fused or partially fused, and comprising from 5 to 6 members selected from the group consisting of C, CH, $CH_2$, O, S, CO, N and $NR_{10}$, wherein $R_{10}$ is selected from hydrogen and $(C_1-C_6)$alkyl, each ring being independently unsaturated, saturated or aromatic, and each ring being further optionally substituted with one or more radicals independently selected from the group consisting of: halogen, $(C_1-C_6)$alkyl, $(C_1-C_6)$haloalkyl, $(C_1-C_6)$ alkyloxy, $(C_1-C_6)$thioalkyl, $(C_2-C_6)$alkylcarbonyl, $(C_2-C_6)$ alkylcarbonyloxy, $(C_2-C_6)$alkyloxycarbonyl, a radical of formula $Si((C_1-C_6)$alkyl$)_3$, $(C_2-C_6)$alkylcarbonylamino, $(C_2-C_6)$alkylaminocarbonyl, cyano, an aldehyde group, nitro, and wherein when the ring system comprises at least one carbon-carbon double bond, the carbon atoms forming a double bond can further be substituted with a radical of formula (II) with the condition that the carbon atom forming the double bond adjacent to the carbon atom substituted with a radical of formula (II) is substituted with hydrogen; to obtain a partially hydrogenated polyacene of formula (III):

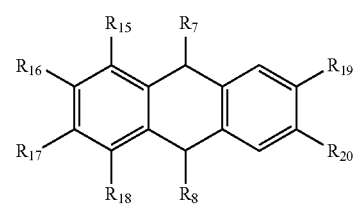

(III)

wherein the $R_{15}$, $R_{16}$, $R_{17}$, $R_{18}$, $R_{19}$, $R_{20}$ have the same meanings as $R_1$, $R_2$, $R_3$, $R_4$, $R_5$, $R_6$ respectively except when a radical of formula (II) is present in the compound of formula (I) then the diradical of formula (II') is cyclized in a diradical of formula (IV) in the compound of formula (III)

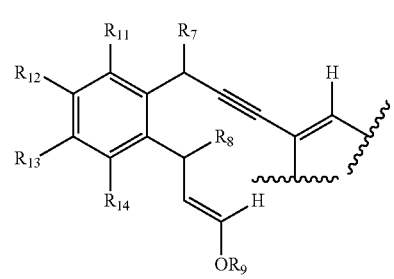

(II')

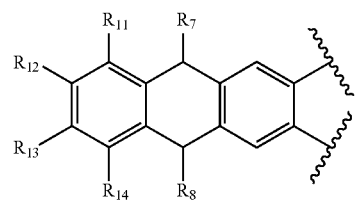

(IV)

The oxidation of the partially hydrogenated polyacene obtained in the first aspect of the invention results in a polyacene compound. The development of a method to obtain polyacene compounds as stable materials for electronic applications operating under ambient conditions is of great interest.

Therefore the second aspect of the invention is a method for the preparation of a polyacene compound comprising:
the step of the method describe above and a final step of (ii) oxidizing the compound of formula (III) to form a compound of formula (VII)

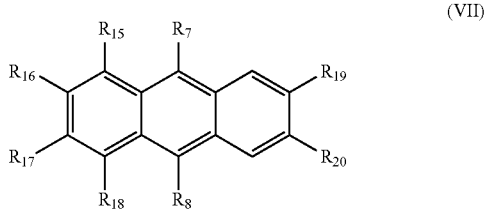

(VII)

wherein $R_7$, $R_8$, $R_{15}$, $R_{16}$, $R_{17}$, $R_{18}$, $R_{19}$ and $R_{20}$ are as defined above except the diradical of formula (IV) in the compound of formula (III), which is replaced by a diradical of formula (VIII) in the compound of formula (VII)

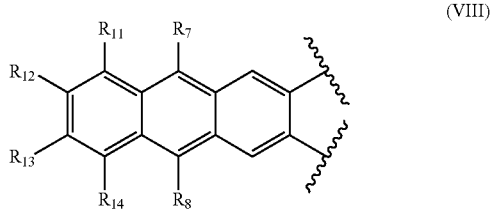

(VIII)

The present invention also describes a new structure of 1,7 enynes.

Therefore the third aspect of the invention is a compound of formula (I')

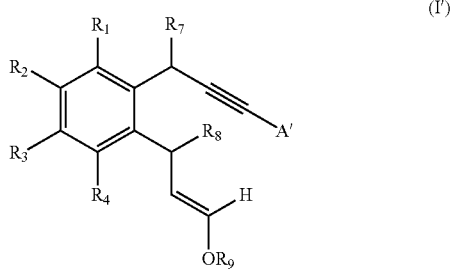

(I')

wherein A' is H or a radical of formula —$CR_5$=$CHR_6$ wherein $R_1$ to $R_9$ are as defined above.

The last aspect of the invention relates to the use of the compound of formula (I') as precursor of the partially hydrogenated polyacene of formula (III).

DETAILED DESCRIPTION OF THE INVENTION

As mentioned above, the first aspect of the present invention relates to a method for the preparation of a partially hydrogenated polyacene.

In the Present Description:

The term "halogen" refers to iodine, bromine, chlorine and fluorine.

The term "alkyl", alone or in combination, refers to a straight-chain or branched-chain alkyl group having the indicated number of carbon atoms. For example, $C_{1-6}$ alkyl refers to an alkyl group having from one to six carbon atoms with the remaining valences occupied by hydrogen atoms. Examples of straight-chain and branched $C_{1-6}$ alkyl group include but are not limited to, methyl, ethyl, propyl, isopropyl, butyl, isobutyl, tert-butyl, the isomeric pentyls, the isomeric hexyls and the like.

The term "alkyloxy" means an alkyl substituent attached to the remainder of a molecule via oxygen, in which the term "alkyl" has the previously given definition. Examples of alkyloxy group include, but are not limited to, methoxy, ethoxy, n-propoxy, isopropoxy, n-butoxy, isobutoxy, sec-butoxy and tert-butoxy.

The term "thioalkyl" refers to an alkyl substituent attached to the remainder of a molecule via sulfur in which the term "alkyl" has the previously given definition. Examples of thioalkyl group include, but are not limited to, methylthio, ethylthio, propylthio, isopropylthio, and n-butylthio.

The term "alkylcarbonyl" embraces groups having a carbonyl radical substituted with an alkyl radical, in which the term "alkyl" has the previously given definition. It is mentioned that if the alkyl have for example 1 to 5 carbon, then the number of carbon atoms of alkylcarbonyl are altogether 2 to 6. Examples of such radicals include, but are not limited to, methylcarbonyl and ethylcarbonyl.

The term "alkylcarbonyloxy" includes alkyl as defined above bonded to carbonyl bonded to oxygen. Examples of alkylcarbonyloxy group include, but are not limited to, acetate, propionate and t-butylcarbonyloxy.

The term "alkyloxycarbonyl" means a radical containing an alkyloxy radical, as defined above, attached via the oxygen atom to a carbonyl radical. Examples of such radicals include, but are not limited to, substituted or unsubstituted methoxycarbonyl, ethoxycarbonyl, propoxycarbonyl, butoxycarbonyl and hexyloxycarbonyl.

The term "alkylcarbonylamino" refers to a group of formula —NH(CO)R where R is an alkyl, in which the term "alkyl" has the previously given definition. Examples of such radicals include, but are not limited to, acetylamino, indole-2-ylacetylamino.

The term "alkylaminocarbonyl" refers to a group of formula RNHCO— wherein R is an alkyl, in which the term "alkyl" has the previously given definition. Example is methylaminocarbonyl.

The term "aryl" means, unless otherwise stated, a polyunsaturated hydrocarbon group which can be a single ring or multiple rings (up to six rings) which are fused together or linked covalently, and which optionally carries one or more substituents as described herein, for example, such as halogen, trifluoromethyl, amino, alkyl, alkyloxy, alkylcarbonyl, cyano, carbamoyl, alkoxycarbamoyl, methylendioxy, carboxy, alkyloxycarbonyl, aminocarbonyl, alkylaminocarbonyl, dialkylaminocarbonyl, hydroxy, nitro and the like. Non-limiting examples of unsubstituted aryl groups include phenyl, naphthyl, phenanthrenyl, anthracenyl and biphenyl. Examples of substituted aryl groups include, but are not limited to phenyl, chlorophenyl, trifluoromethylphenyl, chlorofluorophenyl, and aminophenyl.

The term "heteroaryl", alone or in combination, refers to an aromatic 5- to 10-membered aromatic heterocycle which contains one or more, preferably one or two hetero atoms selected from nitrogen, oxygen, and sulfur, wherein nitrogen, sulphur or oxygen are preferred. The heteroaryl may be substituted on one or more carbon atoms as defined herein, for example with substituents such as halogen, alkyl, alkoxy, cyano, haloalkyl.

In the present invention the phrase, "with the condition that when one or more of $R_1$, $R_2$, $R_3$ and $R_4$ is a radical of formula (II) at least one carbon atom adjacent to the carbon atom bearing a radical of formula (II) is substituted with hydrogen" means that when $R_1$ is a radical of formula (II) then $R_2$ is H; when $R_2$ is a radical of formula (II) then at least one of $R_1$ and $R_3$ is H; when $R_3$ is a radical of formula (II) then at least one of $R_2$ and $R_4$ is H; when $R_4$ is a radical of formula (II) then $R_3$ is H.

In a preferred embodiment of the first aspect of the invention, each of $R_{11}$, $R_{12}$, $R_{13}$ and $R_{14}$, which may be the same or different, is independently selected from the group consisting of: hydrogen, halogen, straight chain or branched $(C_1\text{-}C_6)$alkyl, $(C_1\text{-}C_6)$haloalkyl, $(C_1\text{-}C_6)$alkyloxy, $(C_1\text{-}C_6)$thioalkyl, $(C_2\text{-}C_6)$alkylcarbonyl, $(C_2\text{-}C_6)$alkylcarbonyloxy, $(C_2\text{-}C_6)$alkyloxycarbonyl, a radical of formula $Si((C_1\text{-}C_6)\text{alkyl})_3$, $(C_2\text{-}C_6)$alkylcarbonylamino, $(C_2\text{-}C_6)$alkylaminocarbonyl, an aldehyde group, cyano, nitro, a $(C_6\text{-}C_{20})$aryl optionally substituted at one or more positions with a radical selected from the group consisting of halogen, $(C_1\text{-}C_6)$alkyl, $(C_1\text{-}C_6)$haloalkyl, $(C_1\text{-}C_6)$alkyloxy, $(C_1\text{-}C_6)$thioalkyl, $(C_2\text{-}C_6)$alkylcarbonyl, $(C_2\text{-}C_6)$alkylcarbonyloxy, $(C_2\text{-}C_6)$alkyloxycarbonyl, a radical of formula $Si((C_1\text{-}C_6)\text{alkyl})_3$, $(C_2\text{-}C_6)$alkylcarbonylamino, $(C_2\text{-}C_6)$alkylaminocarbonyl, cyano, nitro, and an aldehyde group and a $(C_5\text{-}C_{20})$heteroaryl optionally substituted at one or more positions with a radical selected from the group consisting of halogen, $(C_1\text{-}C_6)$alkyl, $(C_1\text{-}C_6)$haloalkyl, $(C_1\text{-}C_6)$alkyloxy, $(C_1\text{-}C_6)$thioalkyl, $(C_2\text{-}C_6)$alkylcarbonyl, $(C_2\text{-}C_6)$alkylcarbonyloxy, $(C_2\text{-}C_6)$alkyloxycarbonyl, a radical of formula $Si((C_1\text{-}C_6)\text{alkyl})_3$, $(C_2\text{-}C_6)$alkylcarbonylamino, $(C_2\text{-}C_6)$alkylaminocarbonyl, cyano, nitro, and an aldehyde group; or, alternatively, one, two or three of the pairs $R_{11}$ and $R_{12}$, $R_{12}$ and $R_{13}$, and $R_{13}$ and $R_{14}$, together with the carbon atoms to which they are attached, form a ring system comprising 1 to 5 rings, each ring being isolated, fused or partially fused, and comprising from 5 to 6 members selected from the group consisting of: C, CH, $CH_2$, CO, O, S, N and $NR_{10}$, wherein $R_{10}$ is selected from hydrogen and $(C_1\text{-}C_6)$alkyl, each ring being independently unsaturated, saturated or aromatic; and each ring being further optionally substituted with one or more radicals selected from the group consisting of: halogen, $(C_1\text{-}C_6)$alkyl, $(C_1\text{-}C_6)$haloalkyl, $(C_1\text{-}C_6)$alkyloxy, $(C_1\text{-}C_6)$thioalkyl, $(C_2\text{-}C_6)$alkylcarbonyl, $(C_2\text{-}C_6)$alkylcarbonyloxy, $(C_2\text{-}C_6)$alkyloxycarbonyl, a radical of formula $Si((C_1\text{-}C_6)\text{alkyl})_3$, $(C_2\text{-}C_6)$alkylcarbonylamino, $(C_2\text{-}C_6)$alkylaminocarbonyl, cyano, and aldehyde group, and nitro.

In a particular embodiment, optionally in combination with one or more of the embodiments described above or below, each of $R_1$, $R_2$, $R_3$ and $R_4$, which may be the same or different, is independently selected from the group consisting of: hydrogen, halogen, straight chain or branched $(C_1\text{-}C_6)$alkyl, $(C_1\text{-}C_6)$haloalkyl, $(C_1\text{-}C_6)$alkyloxy, $(C_1\text{-}C_6)$thioalkyl, $(C_2\text{-}C_6)$alkylcarbonyl, $(C_2\text{-}C_6)$alkylcarbonyloxy, $(C_2\text{-}C_6)$alkyloxycarbonyl, a radical of formula $Si((C_1\text{-}C_6)\text{alkyl})_3$, $(C_2\text{-}C_6)$alkylcarbonylamino, $(C_2\text{-}C_6)$alkylaminocarbonyl, an aldehyde group, cyano, nitro, a $(C_6\text{-}C_{20})$aryl optionally substituted at one or more positions with a radical selected from the group consisting of: halogen, $(C_1\text{-}C_6)$alkyl, $(C_1\text{-}C_6)$haloalkyl, $(C_1\text{-}C_6)$alkyloxy, $(C_1\text{-}C_6)$thioalkyl, $(C_2\text{-}C_6)$alkylcarbonyl, $(C_2\text{-}C_6)$alkylcarbonyloxy, $(C_2\text{-}C_6)$alkyloxycarbonyl, a radical of formula $Si((C_1\text{-}C_6)\text{alkyl})_3$, $(C_2\text{-}C_6)$alkylcarbonylamino, $(C_2\text{-}C_6)$alkylaminocarbonyl, cyano, nitro, and an aldehyde group; and a $(C_5\text{-}C_{20})$heteroaryl optionally substituted at one or more positions with a radical selected from the group consisting of halogen, $(C_1\text{-}C_6)$alkyl, $(C_1\text{-}C_6)$haloalkyl, $(C_1\text{-}C_6)$alkyloxy, $(C_1\text{-}C_6)$thioalkyl, $(C_2\text{-}C_6)$alkylcarbonyl, $(C_2\text{-}C_6)$alkylcarbonyloxy, $(C_2\text{-}C_6)$alkyloxycarbonyl, a radical of formula $Si((C_1\text{-}C_6)\text{alkyl})_3$, $(C_2\text{-}C_6)$alkylcarbonylamino, $(C_2\text{-}C_6)$alkylaminocarbonyl, cyano, nitro, and an aldehyde group; or, alternatively, one, two or three of the pairs $R_1$ and $R_2$, $R_2$ and $R_3$, and $R_3$ and $R_4$, together with the carbon atoms to which they are attached, form a ring system comprising 1 to 5 rings, each ring being isolated, fused or partially fused, and comprising from 5 to 6 members selected from the group consisting of: C, CH, $CH_2$, CO, O, S, N and $NR_{10}$, wherein $R_{10}$ is selected from hydrogen and $(C_1\text{-}C_6)$alkyl, each ring being independently unsaturated, saturated or aromatic; and each ring being further optionally substituted with one or more radicals selected from the group consisting of: halogen, $(C_1\text{-}C_6)$alkyl, $(C_1\text{-}C_6)$haloalkyl, $(C_1\text{-}C_6)$alkyloxy, $(C_1\text{-}C_6)$thioalkyl, $(C_2\text{-}C_6)$alkylcarbonyl, $(C_2\text{-}C_6)$alkylcarbonyloxy, $(C_2\text{-}C_6)$alkyloxycarbonyl, a radical of formula $Si((C_1\text{-}C_6)\text{alkyl})_3$, $(C_2\text{-}C_6)$alkylcarbonylamino, $(C_2\text{-}C_6)$alkylaminocarbonyl, cyano, an aldehyde group and nitro.

In a particular embodiment, optionally in combination with one or more of the embodiments described above or below, each of $R_1$, $R_2$, $R_3$ and $R_4$, which may be the same or different, is independently selected from the group consisting of: hydrogen, halogen, straight chain or branched $(C_1\text{-}C_6)$alkyl, $(C_1\text{-}C_6)$haloalkyl, $(C_1\text{-}C_6)$alkyloxy, $(C_1\text{-}C_6)$thioalkyl, $(C_1\text{-}C_6)$alkylcarbonyl, a radical of formula $Si((C_1\text{-}C_6)\text{alkyl})_3$, an aldehyde group, cyano, nitro; a $(C_6\text{-}C_{20})$aryl optionally substituted at one or more positions with a radical selected from the group consisting of halogen, $(C_1\text{-}C_6)$alkyl, $(C_1\text{-}C_6)$haloalkyl, $(C_1\text{-}C_6)$alkyloxy, and $(C_1\text{-}C_6)$thioalkyl; and a $(C_5\text{-}C_{20})$heteroaryl optionally substituted at one or more positions with a radical selected from the group consisting of halogen, $(C_1\text{-}C_6)$alkyl, $(C_1\text{-}C_6)$haloalkyl, $(C_1\text{-}C_6)$alkyloxy, and $(C_1\text{-}C_6)$thioalkyl; or, alternatively, one, two or three of the pairs $R_1$ and $R_2$, $R_2$ and $R_3$, and $R_3$ and $R_4$, together with the carbon atoms to which they are attached, form a ring system, said ring comprising 1 to 5 rings, each ring being isolated, fused or partially fused, and comprising from 5 to 6 members selected from the group consisting of C, CH, $CH_2$, O, and S, each ring being independently unsaturated, saturated or aromatic; and each ring being further optionally substituted with one or more radicals selected from the group consisting of: halogen, $(C_1\text{-}C_6)$alkyl, $(C_1\text{-}C_6)$haloalkyl, $(C_1\text{-}C_6)$alkyloxy, $(C_1\text{-}C_6)$alkylcarbonyl, a radical of formula $Si((C_1\text{-}C_6)\text{alkyl})_3$, an aldehyde group and nitro.

In a particular embodiment, optionally in combination with one or more of the embodiments described above or below, each of $R_1$, $R_2$, $R_3$ and $R_4$, which may be the same or different, is independently selected from the group consisting of: hydrogen, halogen, straight chain or branched $(C_1\text{-}C_6)$alkyl, $(C_1\text{-}C_6)$haloalkyl, $(C_1\text{-}C_6)$alkyloxy, $(C_1\text{-}C_6)$thioalkyl, $(C_1\text{-}C_6)$alkylcarbonyl, an aldehyde group, cyano, nitro; a $(C_6\text{-}C_{20})$aryl optionally substituted at one or more positions with a radical selected from the group consisting of halogen, $(C_1\text{-}C_6)$alkyl, $(C_1\text{-}C_6)$haloalkyl, $(C_1\text{-}C_6)$alkyloxy, and $(C_1\text{-}C_6)$thioalkyl; and a $(C_5\text{-}C_{20})$heteroaryl optionally substituted at one or more positions with a radical selected from the group consisting of halogen, $(C_1\text{-}C_6)$alkyl, $(C_1\text{-}C_6)$haloalkyl, $(C_1\text{-}C_6)$alkyloxy, and $(C_1\text{-}C_6)$thioalkyl; or, alternatively, one, two or three of the pairs $R_1$ and $R_2$, $R_2$ and $R_3$, and $R_3$ and $R_4$, together with the carbon atoms to which they are attached, form a ring system, said ring comprising 1 to 5 rings, each ring being isolated, fused or partially fused, and comprising from 5 to 6 members selected from the group consisting of C, CH, $CH_2$, O, and S, each ring being independently unsaturated, saturated or aromatic; and each ring being further optionally substituted with one or more radicals selected from the group consisting of: halogen, $(C_1-C_6)$alkyl, $(C_1-C_6)$haloalkyl, $(C_1-C_6)$alkyloxy, and nitro.

In a particular embodiment, optionally in combination with one or more of the embodiments described above or below, each of $R_1$, $R_2$, $R_3$ and $R_4$, which may be the same or different, is independently selected from the group consisting of: hydrogen, halogen, straight chain or branched $(C_1-C_6)$alkyl, $(C_1-C_6)$haloalkyl, $(C_1-C_6)$alkyloxy, $(C_1-C_6)$alkylcarbonyl, and an aldehyde group; and a $(C_6-C_{20})$aryl optionally substituted at one or more positions with a radical selected from the group consisting of halogen, $(C_1-C_6)$alkyl, $(C_1-C_6)$haloalkyl, and $(C_1-C_6)$alkyloxy; or, alternatively, one, two or three of the pairs $R_1$ and $R_2$, $R_2$ and $R_3$, and $R_3$ and $R_4$, together with the carbon atoms to which they are attached, form a ring system, said ring comprising 1 to 5 aromatic rings, each ring being isolated or fused, and comprising from 5 to 6 members selected from the group consisting of C, CH, O, and S, and each ring being further optionally substituted with one or more radicals selected from the group consisting of: halogen, $(C_1-C_6)$alkyl, $(C_1-C_6)$haloalkyl, $(C_1-C_6)$alkyloxy, and nitro.

In a particular embodiment, optionally in combination with one or more of the embodiments described above or below, each of $R_1$, $R_2$, $R_3$ and $R_4$, which may be the same or different, is independently selected from the group consisting of: hydrogen, straight chain or branched $(C_1-C_6)$alkyl, and $(C_1-C_6)$haloalkyl; or, alternatively, one, two or three of the pairs $R_1$ and $R_2$, $R_2$ and $R_3$, and $R_3$ and $R_4$, together with the carbon atoms to which they are attached, form a ring system, said ring comprising 1 to 3 aromatic rings, each ring being isolated, or fused, and comprising 6 members selected from the group consisting of C, and CH.

In a particular embodiment, optionally in combination with one or more of the embodiments described above or below, each of $R_1$, $R_2$, $R_3$ and $R_4$ represent hydrogen; or, alternatively, one of the pairs selected from $R_1$ and $R_2$, and $R_2$ and $R_3$, together with the carbon atoms to which they are attached, form a phenyl ring.

In a particular embodiment, optionally in combination with one or more of the embodiments described above or below, $R_5$ and $R_6$ are each independently selected from the group consisting of: hydrogen, straight chain or branched $(C_1-C_6)$alkyl, $(C_1-C_6)$haloalkyl, a $(C_6-C_{20})$aryl optionally substituted at one or more positions with a radical selected from the group consisting of halogen, $(C_1-C_6)$alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)alkyl)_3$, $(C_2-C_6)$alkylcarbonylamino, $(C_2-C_6)$alkylaminocarbonyl, cyano, nitro, and an aldehyde group, and a $(C_5-C_{20})$heteroaryl optionally substituted at one or more positions with a radical selected from the group consisting of: halogen, $(C_1-C_6)$alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)alkyl)_3$, $(C_2-C_6)$alkylcarbonylamino, $(C_2-C_6)$alkylaminocarbonyl, cyano, nitro, and an aldehyde group; or, alternatively, $R_5$ and $R_6$, together with the carbon atoms to which they are attached, form a ring system comprising 1 to 10 rings, each ring being isolated, fused or partially fused, and comprising from 5 to 6 members selected from the group consisting of C, CH, CH$_2$, O, S, N and NR$_{10}$, wherein R$_{10}$ is selected from hydrogen and $(C_1-C_6)$alkyl, each ring being independently unsaturated, saturated or aromatic, and each ring being further optionally substituted with one or more radicals independently selected from the group consisting of: halogen, $(C_1-C_6)$alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)alkyl)_3$, $(C_2-C_6)$alkylcarbonylamino, $(C_2-C_6)$alkylaminocarbonyl, cyano, an aldehyde group, nitro, and wherein when the ring system comprises at least one carbon-carbon double bond, the carbon atoms forming a double bond can further be substituted with a radical of formula (II) with the condition that the carbon atom forming the double bond adjacent to the carbon atom substituted with a radical of formula (II) is substituted with hydrogen.

In a particular embodiment, optionally in combination with one or more of the embodiments described above or below, $R_5$ and $R_6$ are each independently selected from the group consisting of: hydrogen, straight chain or branched $(C_1-C_6)$alkyl, a $(C_6-C_{20})$aryl optionally substituted at one or more positions with a radical selected from the group consisting of halogen, $(C_1-C_6)$alkyl, $(C_1-C_6)$alkyloxy, $(C_2-C_6)$alkylcarbonyl, a radical of formula $Si((C_1-C_6)alkyl)_3$, and an aldehyde group; or, alternatively, $R_5$ and $R_6$, together with the carbon atoms to which they are attached, form a ring system comprising 1 to 10 rings, each ring being isolated, fused or partially fused, and comprising from 5 to 6 members selected from the group consisting of C, CH, CH$_2$, CO, O, S, N and NR$_{10}$, wherein R$_{10}$ is selected from hydrogen and $(C_1-C_6)$alkyl, each ring being independently unsaturated, saturated or aromatic, and each ring being further optionally substituted with one or more radicals independently selected from the group consisting of: halogen, $(C_1-C_6)$alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)alkyl)_3$, $(C_2-C_6)$alkylcarbonylamino, $(C_2-C_6)$alkylaminocarbonyl, cyano, an aldehyde group, nitro, and wherein when the ring system comprises at least one carbon-carbon double bond, the carbon atoms forming a double bond can further be substituted with a radical of formula (II) with the condition that the carbon atom forming the double bond adjacent to the carbon atom substituted with a radical of formula (II) is substituted with hydrogen.

In a particular embodiment, optionally in combination with one or more of the embodiments described above or below, $R_5$ and $R_6$, together with the carbon atoms to which they are attached, form a ring system comprising 1 to 5 rings, each ring being isolated, fused or partially fused, and comprising from 5 to 6 members selected from the group consisting of C, CH, CH$_2$, CO, O, S, N and NR$_{10}$, wherein R$_{10}$ is selected from hydrogen and $(C_1-C_6)$alkyl, each ring being independently unsaturated, saturated or aromatic, and each ring being further optionally substituted with one or more radicals independently selected from the group consisting of: halogen, $(C_1-C_6)$alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)alkyl)_3$, $(C_2-C_6)$alkylcarbonylamino, $(C_2-C_6)$alkylaminocarbonyl, cyano, an aldehyde group, nitro, and wherein when the ring system comprises at least one carbon-carbon double bond, the carbon atoms forming a double bond can further be substituted with a radical of formula (II) with the condition that the carbon atom forming the double bond adjacent to the carbon atom substituted with a radical of formula (II) is substituted with hydrogen.

In a particular embodiment, optionally in combination with one or more of the embodiments described above or below, $R_5$ and $R_6$, together with the carbon atoms to which they are attached, form a ring system comprising 1 to 5 aromatic rings, each ring being isolated, fused or partially fused, and comprising from 5 to 6 members selected from the group consisting of C, CH, CO, O, S, N and $NR_{10}$, wherein $R_{10}$ is selected from hydrogen and $(C_1$-$C_6)$alkyl and each ring being further optionally substituted with one or more radicals independently selected from the group consisting of halogen, $(C_1$-$C_6)$alkyl, $(C_1$-$C_6)$haloalkyl, $(C_1$-$C_6)$alkyloxy, $(C_1$-$C_6)$thioalkyl, $(C_2$-$C_6)$alkylcarbonyl, $(C_2$-$C_6)$alkylcarbonyloxy, $(C_2$-$C_6)$alkyloxycarbonyl, a radical of formula $Si((C_1$-$C_6)$alkyl$)_3$, $(C_2$-$C_6)$alkylcarbonylamino, $(C_2$-$C_6)$alkylaminocarbonyl, cyano, an aldehyde group, nitro, and a radical of formula (II) with the condition that the carbon atom forming the double bond adjacent to the carbon atom substituted with a radical of formula (II) is substituted with hydrogen.

In a particular embodiment, optionally in combination with one or more of the embodiments described above or below, $R_5$ and $R_6$, together with the carbon atoms to which they are attached, form a ring system comprising 1 to 5 aromatic rings, each ring being isolated, fused or partially fused, and comprising from 5 to 6 members selected from the group consisting of C, CH, and S, and each ring being further optionally substituted with one or more radicals independently selected from the group consisting of halogen, $(C_1$-$C_6)$alkyl, $(C_1$-$C_6)$haloalkyl, $(C_1$-$C_6)$alkyloxy, $(C_2$-$C_6)$alkylcarbonyl, a radical of formula $Si((C_1$-$C_6)$alkyl$)_3$, an aldehyde group, and a radical of formula (II) with the condition that the carbon atom forming the double bond adjacent to the carbon atom substituted with a radical of formula (II) is substituted with hydrogen.

In a particular embodiment, optionally in combination with one or more of the embodiments described above or below, $R_5$ and $R_6$, together with the carbon atoms to which they are attached, form a ring system selected from benzene, naphthalene, phenanthrene, biphenyl, thiophene, benzothiophene and 5'-phenyl-1,1':3',1''-terphenyl, wherein said ring system is further optionally substituted with one or more radicals independently selected from the group consisting of bromo, fluoro, iodo, methyl, methoxy, trimethylsilyl, acetyl, an aldehyde group, and a radical selected from the group consisting of the radicals of formula (IIa), (IIb) and (IIc)

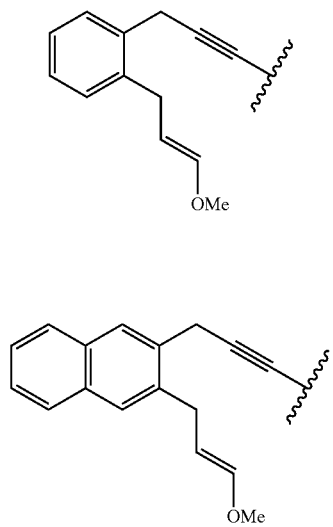

(IIa)

(IIb)

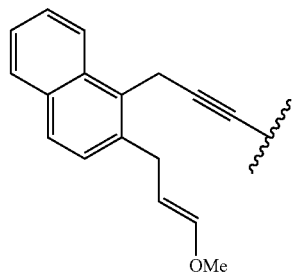

(IIc)

with the condition that the carbon atom of the ring system adjacent to the carbon atom substituted with a radical of formula (IIa), or alternatively (IIb), or alternatively (IIc) is substituted with hydrogen.

In a particular embodiment, optionally in combination with one or more of the embodiments described above or below, $R_5$ and $R_6$, together with the carbon atoms to which they are attached, form a ring system radical selected from the group consisting of

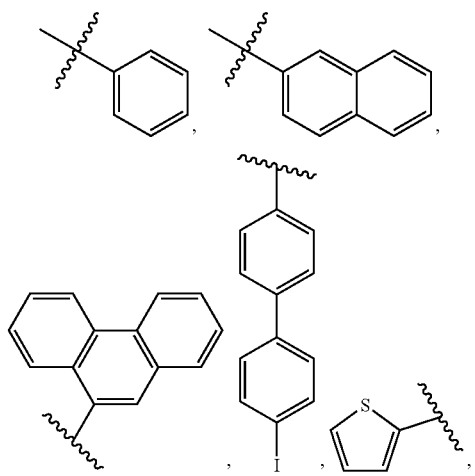

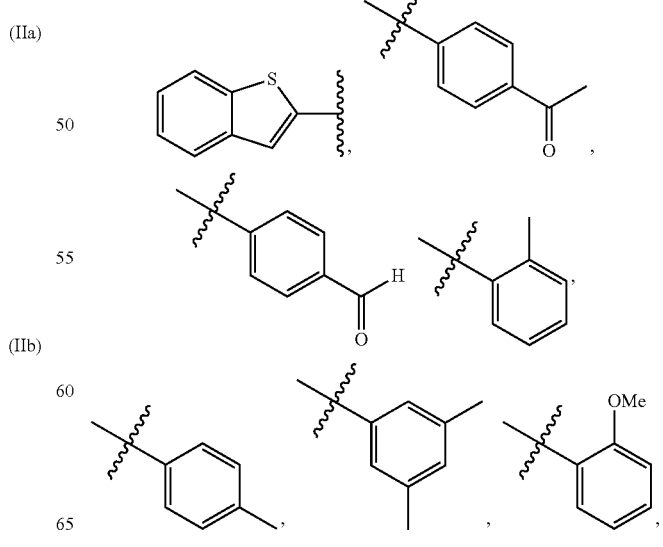

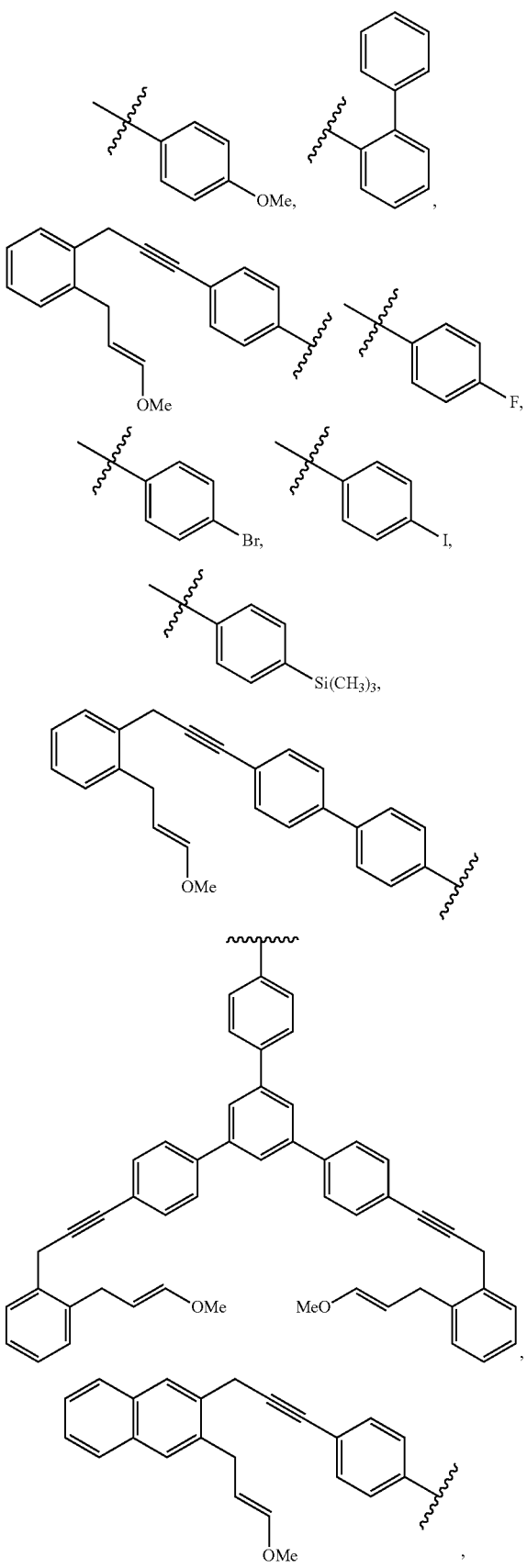

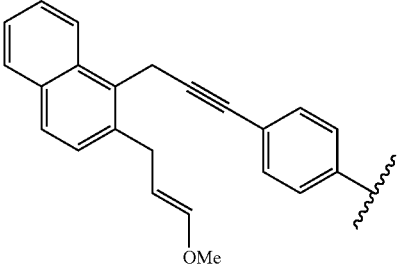

In a particular embodiment, optionally in combination with one or more of the embodiments described above or below, $R_7$ is hydrogen.

In a particular embodiment, optionally in combination with one or more of the embodiments described above or below, $R_8$ is hydrogen.

In a particular embodiment, optionally in combination with one or more of the embodiments described above or below, $R_9$ is selected from the group consisting of methyl, ethyl, propyl, iso-propyl.

In a particular embodiment, optionally in combination with one or more of the embodiments described above or below, $R_9$ is methyl.

In a particular embodiment, optionally in combination with one or more of the embodiments described above or below, $R_{11}$, $R_{12}$, $R_{13}$ and $R_{14}$ represent the same groups as $R_1$, $R_2$, $R_3$ and $R_4$ as defined in any of the embodiments described above or below.

In a particular embodiment, optionally in combination with one or more of the embodiments described above or below, $R_{15}$, $R_{16}$, $R_{17}$, $R_{18}$, $R_{19}$, $R_{20}$ have the same meanings as $R_1$, $R_2$, $R_3$, $R_4$, $R_5$, $R_6$ respectively as defined in any of the embodiments described above or below, except when a radical of formula (II) is present in the compound of formula (I) then the diradical of formula (II') is replaced by a diradical of formula (IV) in a compound of formula (III) and by a diradical of formula (VIII) in a compound of formula (VII)

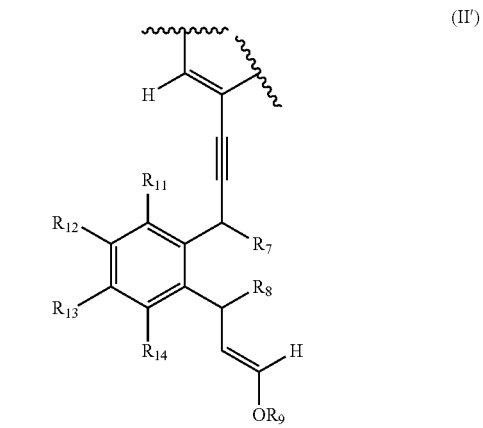

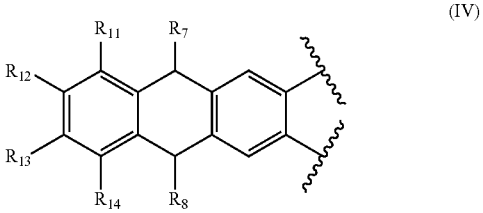

-continued

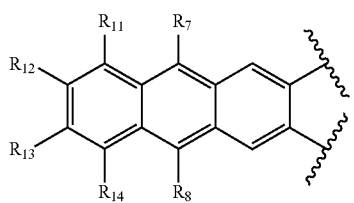

(VIII)

More preferably each of $R_1$, $R_2$, $R_3$ and $R_4$, which may be the same or different, is independently selected from the group consisting of: hydrogen, halogen, straight chain or branched $(C_1-C_6)$alkyl, $(C_1-C_6)$haloalkyl, $(C_1-C_6)$alkyloxy, $(C_1-C_6)$thioalkyl, $(C_1-C_6)$alkylcarbonyl, an aldehyde group, cyano, nitro; a $(C_6-C_{20})$aryl optionally substituted at one or more positions with a radical selected from the group consisting of halogen, $(C_1-C_6)$alkyl, $(C_1-C_6)$haloalkyl, $(C_1-C_6)$alkyloxy, and $(C_1-C_6)$thioalkyl; and a $(C_5-C_{20})$heteroaryl optionally substituted at one or more positions with a radical selected from the group consisting of halogen, $(C_1-C_6)$alkyl, $(C_1-C_6)$haloalkyl, $(C_1-C_6)$alkyloxy, and $(C_1-C_6)$thioalkyl; or, alternatively, one, two or three of the pairs $R_1$ and $R_2$, $R_2$ and $R_3$, and $R_3$ and $R_4$, together with the carbon atoms to which they are attached, form a ring system, said ring comprising 1 to 5 rings, each ring being isolated, fused or partially fused, and comprising from 5 to 6 members selected from the group consisting of C, CH, CH$_2$, O, and S, each ring being independently unsaturated, saturated or aromatic; and each ring being further optionally substituted with one or more radicals selected from the group consisting of: halogen, $(C_1-C_6)$alkyl, $(C_1-C_6)$haloalkyl, $(C_1-C_6)$alkyloxy, and nitro; and $R_5$ and $R_6$ are selected from the group consisting of hydrogen, straight chain or branched $(C_1-C_6)$alkyl, and a $(C_6-C_{20})$aryl optionally substituted at one or more positions with a radical selected from the group consisting of halogen, $(C_1-C_6)$alkyl, and $(C_1-C_6)$haloalkyl; or, alternatively, $R_5$ and $R_6$, together with the carbon atoms to which they are attached, form a ring system comprising 1 to 5 aromatic rings, each ring being isolated, fused or partially fused, and comprising from 5 to 6 members selected from the group consisting of C, CH, CO, O, S, N and NR$_{10}$, wherein $R_{10}$ is selected from hydrogen and $(C_1-C_6)$alkyl and each ring being further optionally substituted with one or more radicals independently selected from the group consisting of halogen, $(C_1-C_6)$alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$alkyloxycarbonyl, a radical of formula Si$((C_1-C_6)$alkyl$)_3$, $(C_2-C_6)$alkylcarbonylamino, $(C_2-C_6)$alkylaminocarbonyl, cyano, an aldehyde group, nitro, and a radical of formula (II) with the condition that the carbon atom of the ring system adjacent to the carbon atom substituted with the radical of formula (II) is substituted with hydrogen.

More preferably each of $R_1$, $R_2$, $R_3$ and $R_4$, which may be the same or different, are independently selected from the group consisting of: hydrogen, halogen, straight chain or branched $(C_1-C_6)$alkyl, $(C_1-C_6)$haloalkyl, $(C_1-C_6)$alkyloxy, $(C_1-C_6)$thioalkyl, a $(C_6-C_{20})$aryl optionally substituted at one or more positions with a radical selected from the group consisting of halogen, $(C_1-C_6)$alkyl, $(C_1-C_6)$haloalkyl, $(C_1-C_6)$alkyloxy, and $(C_1-C_6)$thioalkyl; or, alternatively, one, two or three of the pairs $R_1$ and $R_2$, $R_2$ and $R_3$, and $R_3$ and $R_4$, together with the carbon atoms to which they are attached, form a ring system, said ring comprising 1 to 3 rings, each ring being isolated, fused or partially fused, and comprising from 5 to 6 members selected from the group consisting of C, CH, CH$_2$, each ring being independently unsaturated, saturated or aromatic; and each ring being further optionally substituted with one or more radicals selected from the group consisting of: halogen, $(C_1-C_6)$ alkyl, $(C_1-C_6)$haloalkyl, $(C_1-C_6)$alkyloxy; and $R_5$ and $R_6$ are selected from the group consisting of hydrogen, straight chain or branched $(C_1-C_6)$alkyl, and a phenyl optionally substituted at one or more positions with a radical selected from the group consisting of halogen, $(C_1-C_6)$alkyl, and $(C_1-C_6)$haloalkyl; or, alternatively, $R_5$ and $R_6$, together with the carbon atoms to which they are attached, form a ring system comprising 1 to 5 aromatic rings, each ring being isolated or fused, and comprising from 5 to 6 members selected from the group consisting of C, CH, and S and each ring being further optionally substituted with one or more radicals independently selected from the group consisting of: halogen, $(C_1-C_6)$alkyl, $(C_1-C_6)$haloalkyl, $(C_1-C_6)$alkyloxy, $(C_2-C_6)$alkylcarbonyl, a radical of formula Si$((C_1-C_6)$alkyl$)_3$, an aldehyde group, and a radical of formula (II) with the condition that the carbon atom of the ring system adjacent to the carbon atom substituted with the radical of formula (II) is substituted with hydrogen.

More preferably each of $R_1$, $R_2$, $R_3$ and $R_4$, which may be the same or different, are independently selected from the group consisting of: hydrogen, halogen, straight chain or branched $(C_1-C_6)$alkyl, $(C_1-C_6)$haloalkyl, $(C_1-C_6)$alkyloxy, $(C_1-C_6)$thioalkyl, a $(C_6-C_{20})$aryl optionally substituted at one or more positions with a radical selected from the group consisting of halogen, $(C_1-C_6)$alkyl, $(C_1-C_6)$haloalkyl, $(C_1-C_6)$alkyloxy, and $(C_1-C_6)$thioalkyl; or, alternatively, one, two or three of the pairs $R_1$ and $R_2$, $R_2$ and $R_3$, and $R_3$ and $R_4$, together with the carbon atoms to which they are attached, form a ring system, said ring comprising 1 to 3 rings, each ring being isolated, fused or partially fused, and comprising from 5 to 6 members selected from the group consisting of C, CH, CH$_2$, each ring being independently unsaturated, saturated or aromatic; and each ring being further optionally substituted with one or more radicals selected from the group consisting of: halogen, $(C_1-C_6)$ alkyl, $(C_1-C_6)$haloalkyl, $(C_1-C_6)$alkyloxy; and $R_5$ and $R_6$ are selected from the group consisting of hydrogen, straight chain or branched $(C_1-C_6)$alkyl, and a phenyl optionally substituted at one or more positions with a radical selected from the group consisting of halogen, $(C_1-C_6)$alkyl, and $(C_1-C_6)$haloalkyl; or, alternatively, $R_5$ and $R_6$, together with the carbon atoms to which they are attached, form a ring system comprising 1 to 5 aromatic rings, each ring being isolated or fused, and comprising from 5 to 6 members selected from the group consisting of C, CH, and S and each ring being further optionally substituted with one or more radicals independently selected from the group consisting of: halogen, $(C_1-C_6)$alkyl, $(C_1-C_6)$haloalkyl, $(C_1-C_6)$alkyloxy, $(C_2-C_6)$alkylcarbonyl, a radical of formula Si$((C_1-C_6)$alkyl$)_3$, an aldehyde group, and a radical of formula (II) with the condition that the carbon atom of the ring system adjacent to the carbon atom substituted with the radical of formula (II) is substituted with hydrogen.

Particularly preferably each of $R_1$, $R_2$, $R_3$ and $R_4$, which may be the same or different, are independently selected from the group consisting of: hydrogen, straight chain or branched $(C_1-C_6)$alkyl, $(C_1-C_6)$haloalkyl and phenyl; or, alternatively, one, two or three of the pairs $R_1$ and $R_2$, $R_2$ and $R_3$, and $R_3$ and $R_4$, together with the carbon atoms to which they are attached, form a ring system, said ring comprising 1 to 2 aromatic rings, each ring being isolated, or fused, and comprising 6 members selected from the group consisting of C and CH; and $R_5$ and $R_6$ are selected from the group consisting of hydrogen, straight chain or branched $(C_1-C_6)$alkyl, and a phenyl or, alternatively, $R_5$ and $R_6$, together with the carbon atoms to which they are attached, form a ring system selected from benzene, naphthalene, phenantrene, biphenyl, thiophene, benzothiophene and 5'-phenyl-1,1':3',1''-terphenyl, wherein said ring system is further optionally substituted with one or more radicals independently selected from the group consisting of halogen, $(C_1-C_6)$alkyl, $(C_1-C_6)$haloalkyl, $(C_1-C_6)$alkyloxy, $(C_2-C_6)$alkylcarbonyl, a radical of formula $Si((C_1-C_6)alkyl)_3$, an aldehyde group, and a radical of formula (II) with the condition that the carbon atom of the ring system adjacent to the carbon atom substituted with the radical of formula (II) is substituted with hydrogen.

In a preferred embodiment, each of $R_1$, $R_2$, $R_3$ and $R_4$, which may be the same or different, are independently selected from the group consisting of: hydrogen, straight chain or branched $(C_1-C_6)$alkyl, and $(C_1-C_6)$haloalkyl; or, alternatively, one, two or three of the pairs $R_1$ and $R_2$, $R_2$ and $R_3$, and $R_3$ and $R_4$, together with the carbon atoms to which they are attached, form a ring system, said ring comprising 1 to 3 aromatic rings, each ring being isolated, or fused, and comprising 6 members selected from the group consisting of C and CH; and $R_5$ and $R_6$, together with the carbon atoms to which they are attached, form a ring system comprising 1 to 5 rings, each ring being isolated or fused, and comprising from 5 to 6 members selected from the group consisting of C, CH, and S, each ring being aromatic, and each ring being further optionally substituted with one or more radicals independently selected from the group consisting of halogen, $(C_1-C_6)$alkyl, $(C_1-C_6)$haloalkyl, $(C_1-C_6)$alkyloxy, $(C_1-C_6)$alkylcarbonyl, a radical of formula $Si((C_1-C_6)alkyl)_3$, an aldehyde group, and a radical of formula (II) with the condition that the carbon atom of the ring system adjacent to the carbon atom substituted with the radical of formula (II) is substituted with hydrogen.

In an even more preferred embodiment, $R_1$, $R_2$, $R_3$ and $R_4$ represent hydrogen; or, alternatively, one of the pairs selected from $R_1$ and $R_2$, and $R_2$ and $R_3$, together with the carbon atoms to which they are attached, form a phenyl ring; and $R_5$ and $R_6$, together with the carbon atoms to which they are attached, form a ring system selected from benzene, naphthalene, phenantrene, biphenyl, thiophene, benzothiophene and 5'-phenyl-1,1':3',1''-terphenyl, wherein said ring system is further optionally substituted with one or more radicals independently selected from the group consisting of bromo, fluoro, iodo, methyl, methoxy, trimethylsilyl, acetyl, an aldehyde group, and a radical selected from the group consisting of the radicals of formula (IIa), (IIb) and (IIc)

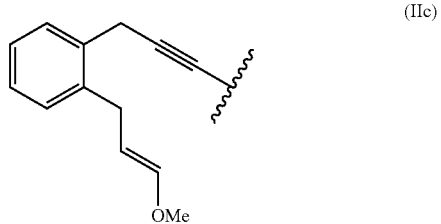

(IIc)

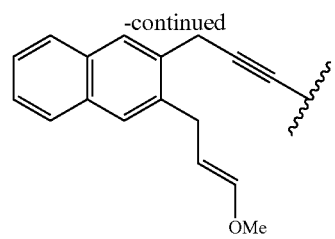

(IIa)

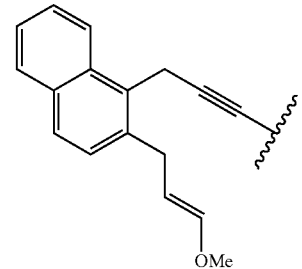

(IIb)

with the condition that the carbon atom of the ring system adjacent to the carbon atom substituted with a radical of formula (IIa), or alternatively (IIb), or alternatively (IIc) is substituted with hydrogen.

In a preferred embodiment of the first aspect and of all the embodiments defined above or below $R_7$ is hydrogen; $R_8$ is hydrogen and $R_9$ is methyl.

In a preferred embodiment of the first aspect of the invention the process of the invention is carried out at a temperature comprised from 0° C. to 80° C. In a preferred embodiment the compound of formula (I) is dissolved in a polar aprotic solvent, more preferably a halogenated solvent, particularly the solvent is selected from: chloroform, dichloromethane, tetrachlorometane and tetrachloroetane. More preferably, the solvent is dichloromethane.

In a preferred embodiment the Au (I) catalyst used in the method described in the first aspect of the invention is a Au(I) complex with one or more ligands. Preferably, it is a Au(I) complex with one or two ligands, the Au(I) complex thus having the general structure: $[L_1-Au(I)]X$ or $[L_1-Au(I)-L_2]X$ wherein each of $L_1$ and $L_2$ is independently a L ligand and X ligands can be covalently bonded to gold or anionic species.

In a more preferred embodiment the L ligand is a member selected from the group of: carbenes, phosphines, sulfonated phosphines, phosphites, phosphinites, phosphonites, arsines, stibines, ethers, ammonia, amines, amides, nitriles, sulfoxides carbonyls, pyridines and thioethers.

In a more preferred embodiment the L ligand is selected from: phosphorous based species, N-heterocyclic carbene, nitriles and thioethers. In a more preferred embodiment the L ligand is selected from: phosphines, phosphites and N-heterocyclic carbenes. In a more preferred embodiment the phosphorous based species is selected from phosphine and phosphite ligand.

In a more preferred embodiment the L ligand is selected from: trimethylphosphine, triethylphosphine, tris(1-methylethyl)phosphine, dimethylphenylphosphine, tris(1,1-dimethylethyl)phosphine, (1,1'-biphenyl)-2-ylbis(1,1-dimethylethyl)phosphine, bis(1,1-dimethylethyl)[2',4',6'-tris(1-methylethyl)[1,1'-biphenyl]-2-yl]phosphine, bis(1,1-dimethylethyl)[3,4,5,6-tetramethyl-2',4',6'-tris(1-methylethyl)[1,1'-biphenyl]-2-yl]phosphine, dicyclohexyl(2',6'-dimethoxy[1,1'-biphenyl]-2-yl)phosphine, [3,6-dimethoxy-2',4',6'-tris(1-methylethyl)[1,1'-biphenyl]-2-yl]

bis(1,1-dimethylethyl)phosphine, methyldiphenylphosphine, triphenylphosphine, tricyclohexylphosphine, (2-methylphenyl)diphenylphosphine, tris(4-methylphenyl)phosphine, [[1,1'-biphenyl]-2-ylbis(1,1-dimethylethyl)phosphine, (1,1-dimethylethyl)phosphine, [[1,1'-biphenyl]-2-yl-dicyclohexylphosphine], [bis(1,1-dimethylethyl)[3,4,5,6-tetramethyl-2',4',6'-tris(1-methylethyl)[1,1'-biphenyl]-2-yl]phosphine, [tris[4-trifluoromethyl)phenyl]phosphine, [tris(2,3,4,5,6-pentafluorophenyl)phosphine, [1,1'-biphenyl]-2-ylbis(tricyclo[3.3.1.1³·⁷]dec-a-yl)phosphine, dicyclohexyl[2',4',6'-tris(1-methylethyl[1,1'-biphenyl]-2-yl]phosphine, dicyclohexyl(2',6'-dimethoxy[1,1'-biphenyl]-2-yl)phosphine, [2',6'-bis(1-methylethoxy)[1,1'-biphenyl]-2-yl]dicyclohexylphosphine, [3,6-dimethoxy-2',4',6'-tris(1-methylethyl)[1,1'biphenyl]-2-yl]bis(1,1-dimethylethyl)phosphine, bis[3,5-bis(trifluoromethyl)phenyl][3,6-dimethoxy-2',4',6'-tris(1-methylethyl)[1,1'-biphenyl]-2-yl]phosphine, (2-biphenyl)di-tert-butylphosphine (JohnPhos), trimethylphosphite, triphenyl phosphite, tris[2,4-bis(1,1-dimethylethyl)phenyl]phosphite, tetrahydrothiophene, benzonitrile, and acetonitrile.

In a particular embodiment the Au(I) catalyst is selected from the catalysts of formula A (Acetonitrile)[(2-biphenyl)di-tert-butylphosphine]gold(I) hexafluoroantimonate; B (Benzonitrile) [1,3-bis(2,6-diisopropylphenyl)imidazol-2-ylidene] gold(I) hexafluoroantimonate and C (Benzonitrile)[tris(2,4-di-tert-butylphenyl)phosphite]gold(I) hexafluoroantimonate.

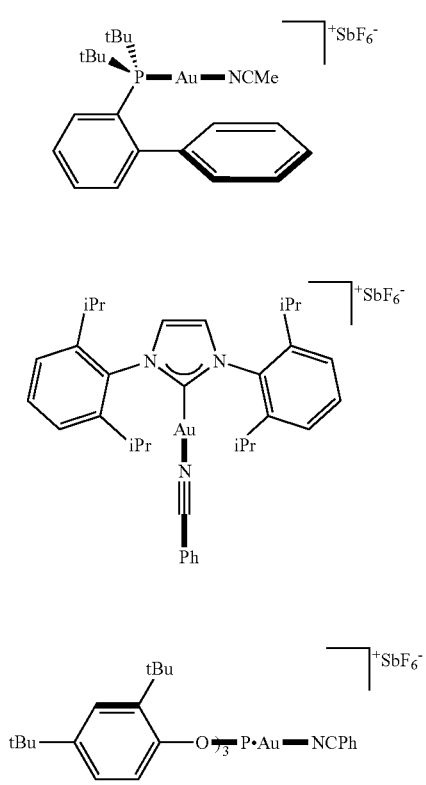

In a preferred embodiment, the Au(I) is a catalyst of formula A (Acetonitrile)[(2-biphenyl)di-tert-butylphosphine]gold(I) hexafluoroantimonate. In another preferred embodiment, the ratio of Au(I) catalyst to compound of formula (I) is comprised from 0.1:100 to 5:100. In a preferred embodiment, the ratio of Au(I) catalyst to compound of formula (I) is comprised from 1:100 to 3:100. In a more preferred embodiment the Au(I) catalyst is a catalyst of formula A (Acetonitrile)[(2-biphenyl)di-tert-butylphosphine]gold(I) hexafluoroantimonate, and the ratio of Au(I) catalyst to compound of formula (I) is 2.5:100.

In a more preferred embodiment the method of the first aspect of the invention further comprises the previous step of producing the compound of formula (I) by reacting the compound of formula (V)

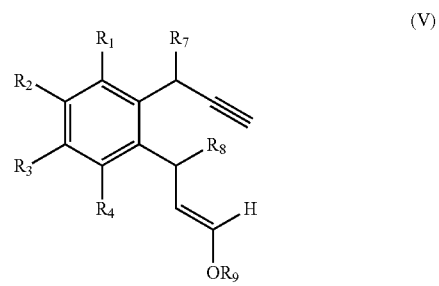

with a compound of formula X—CR$_5$=CHR$_6$ in the presence of a catalyst and a ligand; wherein R1 to R9 are as defined in any of the embodiments above and below and X is a leaving group.

In a preferred embodiment the ratio between the compound of formula (VI) and the compound of formula X—CR$_5$=CHR$_6$ is comprised between 1:1 to 1:4.

The leaving group mentioned is not particularly limited. Preferred examples thereof include halogen atoms such as iodine, bromine, and chlorine; oxygen-atom-bonding type substituents such as sulfonate groups (e.g., methylsulfonate and trifluoromethylsulfonate, phenylsulfonate and tosylate). More preferred are halogen atoms. Especially preferred is a iodine atom. In a more preferred embodiment the catalyst mentioned is a palladium catalyst and the ligand is a phosphorus ligand. Particularly the catalyst used is (PdCl$_2$(PPh$_3$)$_2$) in the presence of CuI.

In a particular embodiment the compound of formula (III) obtained in the first aspect of the invention is selected from: 5,12 dihydrotetracene; 8,13 dihydrobenzo[a]tetracene; 10,15-dihydrodibenzo[a,c]tetracene, 7-methyl-5,12-dihydrotetracene, 8-methyl-5,12-dihydrotetracene; 7,9 dimethyl-5,12-dihydrotetracene; 7-methoxy-5,12-dihydrotetracene; 8-methoxy-5,12-dihydrotetracene; 1-(6,11-dihydrotetracen-2-yl)ethan-1-one, 6,11-dihydrotetracen-2-carbaldehyde; 8-fluoro-5,12 dihydrotetracene; 8-bromo-5,12 dihydrotetracene; 8-iodo-5,12 dihydrotetracene; 6,11 dihydrotetracene-2-yl)trimethylsilane; 7-phenyl-5,12 dihydrotetracene; 8-(4-iodophenyl) 5,12 dihydrotetracene; 5,10-dihydroanthra[2,3-b]thiophene; 7,12-dihydroanthra[2,3-b]benzo[d]thiophene; 7,16-dihydrodibenzo[a, j]tetracene; 6,13 dihydropentacene; 6,6',11,11'-tetrahydro-2,2'-bitetracene; 5,9,14,18 tetrahydroheptacene; 1,3,5-tris(6,11-dihydrotetracen-2-yl)benzene; 7,11,18,22-tetrahydrodibenzol[a,p]heptacene and 6,10,17,21-tetrahydrononoacene.

In a preferred embodiment of the invention and of all the embodiments defined above or below the method comprises a final step of (ii) oxidizing the compound of formula (III) to form a compound of formula (VII)

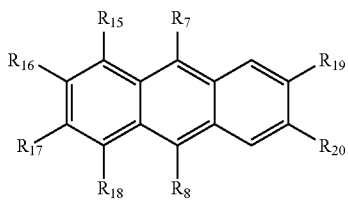
(VII)

wherein $R_7$, $R_8$, $R_{15}$, $R_{16}$, $R_{17}$, $R_{18}$, $R_{19}$ and $R_{20}$ are as defined above except the diradical of formula (IV) in the compound of formula (III), which is replaced by a diradical of formula (VIII) in the compound of formula (VII)

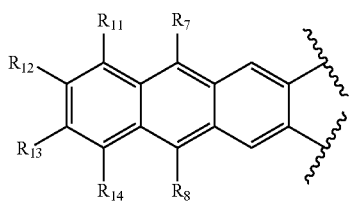
(VIII)

Preferably the oxidation step of the second aspect of the invention is carried out in the presence of an oxidant, preferably selected from Pd/C, o-chloranil or DDQ (2,3-dichloro-5,6-dicyano-1,4-benzoquinone). More preferably the oxidation step is carried out via on-surface (cyclo) dehydrogenation process.

The present invention also describes a new structure of 1,7 enynes of formula (I') as described above and in a particular embodiment the compound of formula (I') is selected from the group: 1-(3-methoxyallyl)-2-(prop-2-yn-1-yl)benzene; 2-(3-methoxyallyl)-3-(prop-2-yn-1-yl) naphthalene; 2-(3methoxyallyl)-1-(prop-2-yn-1-yl)naphthalene; 1-(3-Methoxyallyl)-2-(3-phenylprop-2-yn-1-yl)benzene; 2-(3-(2-(3-Methoxyallyl)phenyl)prop-1-yn-1-yl)naphthalene;
9-(3-(2-(3-Methoxyallyl)phenyl)prop-1-yn-1-yl)phenanthrene;
1-(3-Methoxyallyl)-2-(3-(o-tolyl) prop-2-yn-1-yl)benzene;
1-(3-Methoxyallyl)-2-(3-(p-tolyl) prop-2-yn-1-yl)benzene;
1-(3-(2-(3-Methoxyallyl)phenyl)prop-1-yn-1-yl)-3,5-dimethylbenzene;
1-Methoxy-2-(3-(2-(3-methoxyallyl)phenyl) prop-1-yn-1-yl)benzene;
1-(3-Methoxyallyl)-2-(3-(4-methoxyphenyl) prop-2-yn-1-yl)benzene;
1-(4-(3-(2-(3-Methoxyallyl)phenyl)prop-1-yn-1-yl)phenyl) ethan-1-one;
4-(3-(2-(3-Methoxyallyl)phenyl)prop-1-yn-1-yl)benzaldehyde;
1-(3-(4-Fluorophenyl)prop-2-yn-1-yl)-2-(3-methoxyallyl) benzene;
1-(3-(4-Bromophenyl)prop-2-yn-1-yl)-2-(3-methoxyallyl) benzene;
1-(3-(4-Iodophenyl)prop-2-yn-1-yl)-2-(3-methoxyallyl) benzene;
(4-(3-(2-(3-Methoxyallyl)phenyl)prop-1-yn-1-yl)phenyl) trimethylsilane;
2-(3-(2-(3-Methoxyallyl)phenyl)prop-1-yn-1-yl)-1,1'-biphenyl;
4-Iodo-4'-(3-(2-(3-methoxyallyl)phenyl)prop-1-yn-1-yl)-1,1'-biphenyl;
2-(3-(2-(3-Methoxyallyl)phenyl)prop-1-yn-1-yl)thiophene;
2-(3-(2-(3-Methoxyallyl)phenyl)prop-1-yn-1-yl)benzo[b] thiophene;
2-(3-Methoxyallyl)-1-(3-(naphthalen-2-yl)prop-2-yn-1-yl) naphthalene;
2-(3-Methoxyallyl)-3-(3-phenylprop-2-yn-1-yl)naphthalene;
4,4'-Bis(3-(2-(3-methoxyallyl)phenyl)prop-1-yn-1-yl)-1,1'-biphenyl;
(2,5-Bis(3-(2-(3-methoxyallyl)phenyl)prop-1-yn-1-yl)-1,4-phenylene)bis(trimethylsilane);
4,4"-Bis(3-(2-(3-methoxyallyl)phenyl) prop-1-yn-1-yl)-5'-(4-(3-(2-(3-methoxyallyl)phenyl) prop-1-yn-1-yl)phenyl)-1,1':3',1"-terphenyl;
1,4-Bis(3-(2-(3-methoxyallyl)naphthalen-1-yl)prop-1-yn-1-yl)benzene;
1,4-Bis(3-(3-(3-methoxyallyl)naphthalen-2-yl) prop-1-yn-1-yl)benzene.

The invention also relates to a method for the preparation of the compound of formula (I) comprising:
a) reacting the compound (VI)

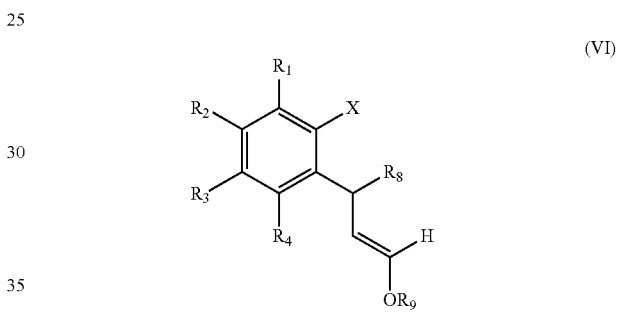
(VI)

with a compound of formula $H_3COCR_7\!\!=\!\!C\!\!=\!\!CH_2$; wherein X is a halogen and wherein $R_1$ to $R_9$ are as defined above to obtain the compound of formula (V);
b) reacting the compound of formula (V)

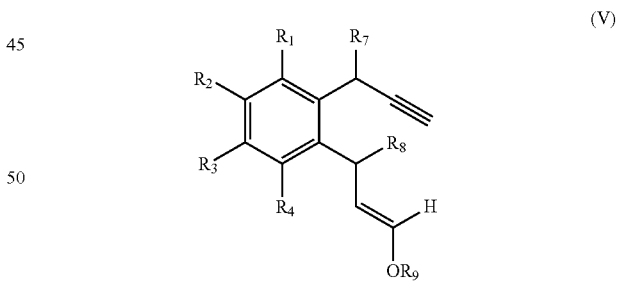
(V)

with a compound of formula $X\!-\!CR_5\!\!=\!\!CHR_6$ in the presence of a catalyst and a ligand; wherein R1 to R9, the catalyst and the ligand are as defined above and X is a leaving group.

Throughout the description and claims the word "comprise" and variations of the word, are not intended to exclude other technical features, additives components, or steps. Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Polyacene Precursors and Preparation Method Thereof
1. Synthesis of enyne precursors
2. Synthesis of 1,7-enynes
3. Gold-catalyzed synthesis of polyhydroacenes
1. Synthesis of Enyne Precursors

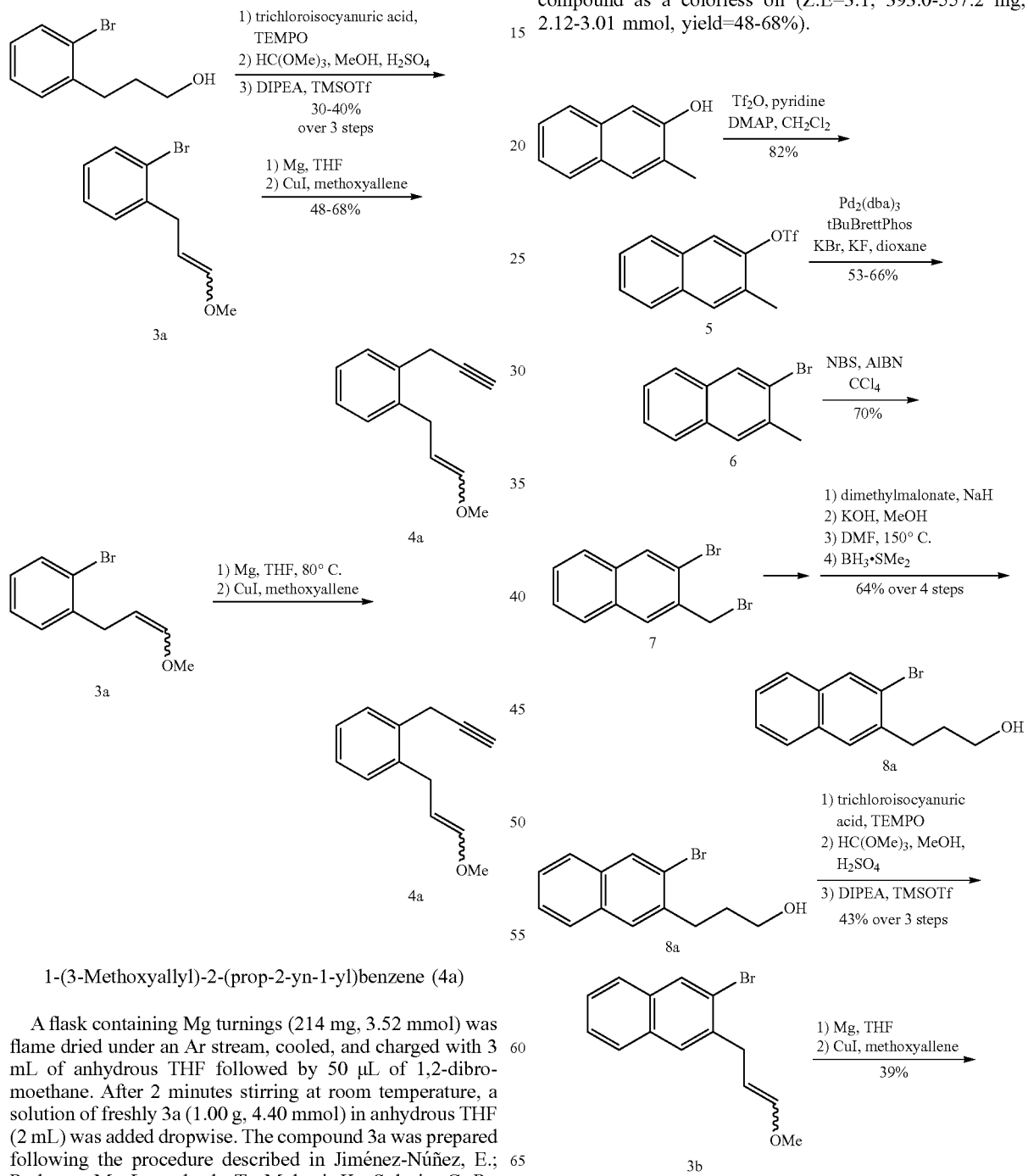

1-(3-Methoxyallyl)-2-(prop-2-yn-1-yl)benzene (4a)

A flask containing Mg turnings (214 mg, 3.52 mmol) was flame dried under an Ar stream, cooled, and charged with 3 mL of anhydrous THF followed by 50 μL of 1,2-dibromoethane. After 2 minutes stirring at room temperature, a solution of freshly 3a (1.00 g, 4.40 mmol) in anhydrous THF (2 mL) was added dropwise. The compound 3a was prepared following the procedure described in Jiménez-Núñez, E.; Raducan, M.; Lauterbach, T.; Molawi, K.; Solorio, C. R.; Echavarren, A. M. *Angew. Chem. Int. Ed.* 2009, 48, 6152-6155. After heating at 80° C. for 1 hour, the reaction was cooled down to room temperature and added over a mixture of CuI (16.8 mg, 0.08 mmol) and methoxyallene (0.74 mL, 8.80 mmol) in anhydrous THF (2 mL). The resulting mixture was heated at 60° C. for 4 hours and then cooled down to room temperature, diluted with EtOAc (10 mL) and quenched by the addition of saturated solution of NaHCO$_3$ (20 mL). The organic layer was separated and the aqueous phase was extracted with EtOAc (20 mL). The combined organic layers were dried over MgSO$_4$, filtered and concentrated under reduced pressure. Purification by column chromatography (pentane/CH$_2$Cl$_2$/NEt$_3$ 90:10:1) gave the title compound as a colorless oil (Z:E=3:1, 393.0-557.2 mg, 2.12-3.01 mmol, yield=48-68%).

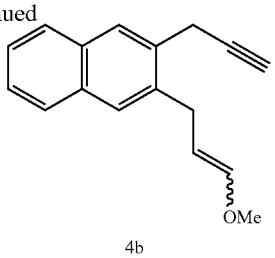

4b

2-(3-Methoxyallyl)-3-(prop-2-yn-1-yl)naphthalene (4b)

Procedure for 4a starting from 3b (240 mg, 0.87 mmol). Colorless oil (80.2 mg, 0.34 mmol, 1:2 E/Z ratio, yield=39%).

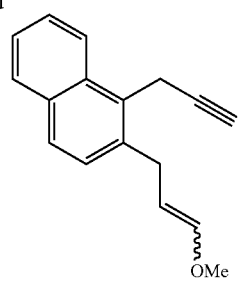

4c

2-(3-Methoxyallyl)-1-(prop-2-yn-1-yl)naphthalene (4c)

Procedure for 4a starting from 3c (500 mg, 1.80 mmol). Colorless oil (178.5 mg, 0.75 mmol, 1:2 E/Z ratio, yield=42%).

2. Synthesis of 1,7-Enynes

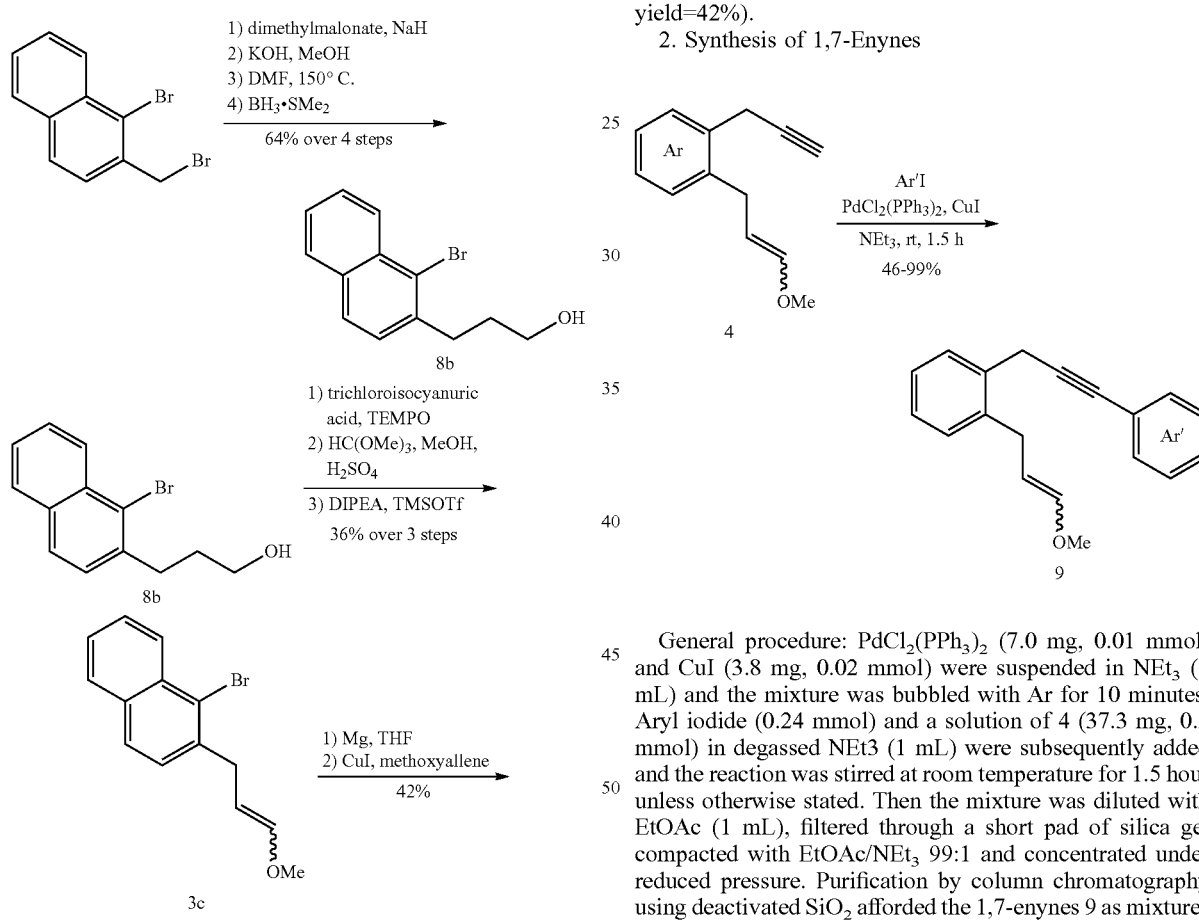

General procedure: $PdCl_2(PPh_3)_2$ (7.0 mg, 0.01 mmol) and CuI (3.8 mg, 0.02 mmol) were suspended in $NEt_3$ (1 mL) and the mixture was bubbled with Ar for 10 minutes. Aryl iodide (0.24 mmol) and a solution of 4 (37.3 mg, 0.2 mmol) in degassed NEt3 (1 mL) were subsequently added and the reaction was stirred at room temperature for 1.5 hour unless otherwise stated. Then the mixture was diluted with EtOAc (1 mL), filtered through a short pad of silica gel compacted with $EtOAc/NEt_3$ 99:1 and concentrated under reduced pressure. Purification by column chromatography using deactivated $SiO_2$ afforded the 1,7-enynes 9 as mixtures of Z:E isomers.

| (4) | Ar'I | (9) | Yield (%) |
|---|---|---|---|
| 4a | iodobenzene | 1-(3-Methoxyallyl)-2-(3-phenylprop-2-yn-1-yl)benzene (9a). | 95 |
| 4a | 2-iodonaphthalene | 2-(3-(2-(3-Methoxyallyl)phenyl)prop-1-yn-1-yl)naphthalene (9b). | 64 |
| 4a | 9-iodophenanthrene | 9-(3-(2-(3-Methoxyallyl)phenyl)prop-1-yn-1-yl)phenanthrene (9c). | 54 |
| 4a | 2-iodotoluene | 1-(3-Methoxyallyl)-2-(3-(o-tolyl)prop-2-yn-1-yl)benzene (9d). | 72 |

-continued

| (4) | Ar'I | (9) | Yield (%) |
|---|---|---|---|
| 4a | 4-iodotoluene | 1-(3-Methoxyallyl)-2-(3-(p-tolyl)prop-2-yn-1-yl)benzene (9e). | 67 |
| 4a | 1-iodo-3,5-dimethylbenzene | 1-(3-(2-(3-Methoxyallyl)phenyl)prop-1-yn-1-yl)-3,5-dimethylbenzene (9f). | 59 |
| 4a | 2-iodoanisole | 1-Methoxy-2-(3-(2-(3-methoxyallyl)phenyl)prop-1-yn-1-yl)benzene (9g). | 86 |
| 4a | 4-iodoanisole | 1-(3-Methoxyallyl)-2-(3-(4-methoxyphenyl)prop-2-yn-1-yl)benzene (9h). | 86 |
| 4a | 4-iodoacetophenone | 1-(4-(3-(2-(3-Methoxyallyl)phenyl)prop-1-yn-1-yl)phenyl)ethan-1-one (9i). | 88 |
| 4a | 4-iodobenzaldehyde | 4-(3-(2-(3-Methoxyallyl)phenyl)prop-1-yn-1-yl)benzaldehyde (9j). | 73 |
| 4a | 1-fluor-4-iodobenzene | 1-(3-(4-Fluorophenyl)prop-2-yn-1-yl)-2-(3-methoxyallyl)benzene (9k). | 99 |
| 4a | 1-bromo-4-iodobenzene | 1-(3-(4-Bromophenyl)prop-2-yn-1-yl)-2-(3-methoxyallyl)benzene (9l). | 88 |
| 4a | 1,4-diiodobenzene | 1-(3-(4-Iodophenyl)prop-2-yn-1-yl)-2-(3-methoxyallyl)benzene (9m). | 55 |
| 4a | 4-iodophenyl)trimethylsilane | (4-(3-(2-(3-Methoxyallyl)phenyl)prop-1-yn-1-yl)phenyl)trimethylsilane (9n). | 82 |
| 4a | 2-iodobiphenyl | 2-(3-(2-(3-Methoxyallyl)phenyl)prop-1-yn-1-yl)-1,1'-biphenyl (9o). | 60 |
| 4a | 4,4'-diiodobiphenyl | 4-Iodo-4'-(3-(2-(3-methoxyallyl)phenyl)prop-1-yn-1-yl)-1,1'-biphenyl (9p). | 46 |
| 4a | 2-iodothiophene | 2-(3-(2-(3-Methoxyallyl)phenyl)prop-1-yn-1-yl)thiophene (9q). | 95 |
| 4a | 2-iodobenzothiophene | 2-(3-(2-(3-Methoxyallyl)phenyl)prop-1-yn-1-yl)benzo[b]thiophene (9r). | 63 |
| 4c | 2-iodonaphthalene | 2-(3-Methoxyallyl)-1-(3-(naphthalen-2-yl)prop-2-yn-1-yl)naphthalene (9s). | 80 |
| 4b | iodobenzene | 2-(3-Methoxyallyl)-3-(3-phenylprop-2-yn-1-yl)naphthalene (9t). | 88 |
| 4a | 4,4'-diiodobiphenyl 2.5 equivalents of 4a | 4,4'-Bis(3-(2-(3-methoxyallyl)phenyl)prop-1-yn-1-yl)-1,1'-biphenyl (9u). | 93 |
| 4a | 1,4-diiodobenzene using 2.5 equivalents of 4a | (2,5-Bis(3-(2-(3-methoxyallyl)phenyl)prop-1-yn-1-yl)-1,4-phenylene)bis(trimethylsilane) (9v). | 88 |
| 4a | 1,3,5-tris(4-iodophenyl)benzene using 4 equivalents of 4a | 4,4''-Bis(3-(2-(3-methoxyallyl)phenyl)prop-1-yn-1-yl)-5'-(4-(3-(2-(3-methoxyallyl)phenyl)prop-1-yn-1-yl)phenyl)-1,1': 3',1''-terphenyl (9w). | 42 |
| 4c | 1,4-diiodobenzene using 2.5 equivalents of 4c | 1,4-Bis(3-(2-(3-methoxyallyl)naphthalen-1-yl)prop-1-yn-1-yl)benzene (9x). | 41 |
| 4b | 1,4-diiodobenzene using 2.5 equivalents of 4b | 1,4-Bis(3-(3-(3-methoxyallyl)naphthalen-2-yl)prop-1-yn-1-yl)benzene (9y). | 84 |

3. Gold-Catalyzed Synthesis of Hydroacenes

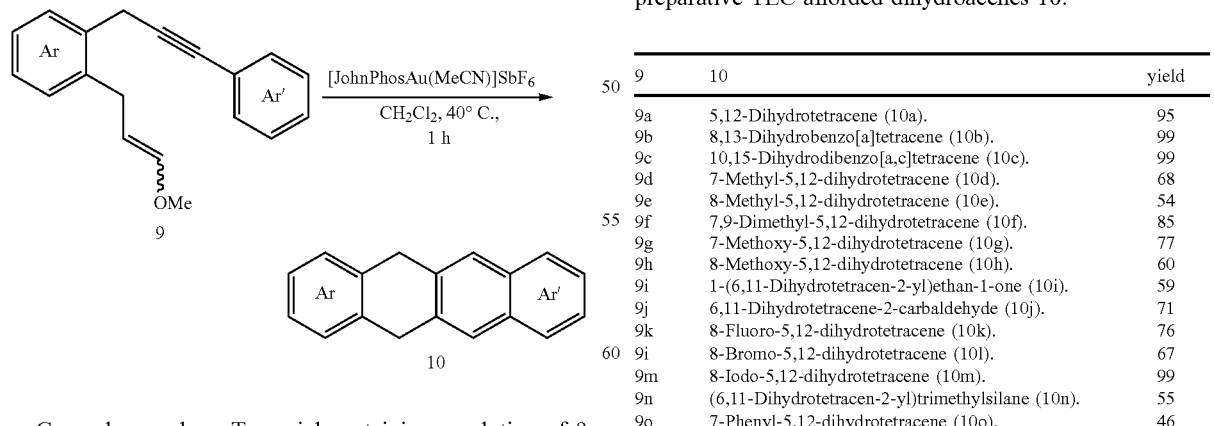

General procedure: To a vial containing a solution of 9 (0.1 mmol) in $CH_2Cl_2$ (1 mL) was added cationic gold catalyst [JohnPhosAu(MeCN)]$SbF_6$ (1.9 mg, 2.5 mol %). The vial was sealed and the reaction was heated to 40° C. for 1 h. After cooling to room temperature a drop of $NEt_3$ was added then the solvents were evaporated under reduced pressure. Unless otherwise stated, purification by silica gel preparative TLC afforded dihydroacenes 10.

| 9 | 10 | yield |
|---|---|---|
| 9a | 5,12-Dihydrotetracene (10a). | 95 |
| 9b | 8,13-Dihydrobenzo[a]tetracene (10b). | 99 |
| 9c | 10,15-Dihydrodibenzo[a,c]tetracene (10c). | 99 |
| 9d | 7-Methyl-5,12-dihydrotetracene (10d). | 68 |
| 9e | 8-Methyl-5,12-dihydrotetracene (10e). | 54 |
| 9f | 7,9-Dimethyl-5,12-dihydrotetracene (10f). | 85 |
| 9g | 7-Methoxy-5,12-dihydrotetracene (10g). | 77 |
| 9h | 8-Methoxy-5,12-dihydrotetracene (10h). | 60 |
| 9i | 1-(6,11-Dihydrotetracen-2-yl)ethan-1-one (10i). | 59 |
| 9j | 6,11-Dihydrotetracene-2-carbaldehyde (10j). | 71 |
| 9k | 8-Fluoro-5,12-dihydrotetracene (10k). | 76 |
| 9i | 8-Bromo-5,12-dihydrotetracene (10l). | 67 |
| 9m | 8-Iodo-5,12-dihydrotetracene (10m). | 99 |
| 9n | (6,11-Dihydrotetracen-2-yl)trimethylsilane (10n). | 55 |
| 9o | 7-Phenyl-5,12-dihydrotetracene (10o). | 46 |
| 9p | 8-(4-Iodophenyl)-5,12-dihydrotetracene (10p). | 71 |
| 9q | 5,10-Dihydroanthra[2,3-b]thiophene (10q). | 93 |
| 9r | 7,12-Dihydroanthra[2,3-b]benzo[d]thiophene (10r). | 88 |
| 9s | 7,16-Dihydrodibenzo[a,j]tetracene (10s). | 61 |

-continued

| 9 | 10 | yield |
|---|---|---|
| 9t | 6,13-Dihydropentacene (10t). | 63 |
| 9u | 6,6',11,11'-Tetrahydro-2,2'-bitetracene (10u). | 77 |
| 9v | 5,9,14,18-Tetrahydroheptacene (10v). | 56 |
| 9w | 1,3,5-Tris(6,11-dihydrotetracen-2-yl)benzene (10w). | 68 |
| 9x | 7,11,18,22-Tetrahydrodibenzo[a,p]heptacene (10x). | 38 |
| 9y | 6,10,17,21-Tetrahydrononacene (10y). | 31 |

What is claimed is:

1. A method for the preparation of a partially hydrogenated polyacene comprising the step of:

contacting a compound of formula (I):

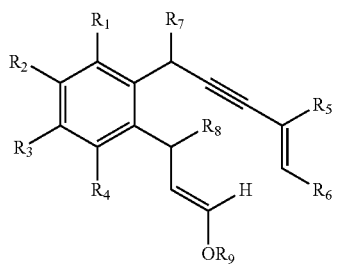

with a catalytically effective amount of a Au(I) catalyst, wherein each of $R_1$, $R_2$, $R_3$ and $R_4$, which may be the same or different, is independently selected from the group consisting of: hydrogen, halogen, straight chain or branched $(C_1-C_6)$alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)alkyl)_3$, $(C_2-C_6)$alkylcarbonylamino, $(C_2-C_6)$alkylaminocarbonyl, an aldehyde group, cyano, nitro, a radical of formula (II):

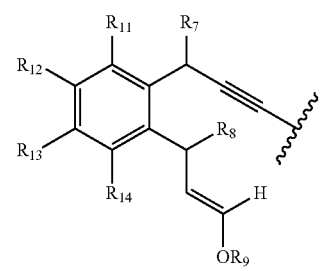

with the condition that when one or more of $R_1$, $R_2$, $R_3$ and $R_4$ is a radical of formula (II) at least one carbon atom adjacent to the carbon atom bearing a radical of formula (II) is substituted with hydrogen; a $(C_6-C_{20})$aryl optionally substituted at one or more positions with a radical selected from the group consisting of: halogen, $(C_1-C_6)$alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)alkyl)_3$, $(C_2-C_6)$alkylcarbonylamino, $(C_2-C_6)$alkylaminocarbonyl, cyano, nitro, an aldehyde group and a radical of formula (II) with the condition that at least one carbon atom adjacent to the carbon atom of the $(C_6-C_{20})$aryl substituted with the radical of formula (II) is substituted with hydrogen; and a $(C_5-C_{20})$heteroaryl optionally substituted at one or more positions with a radical selected from the group consisting of halogen, $(C_1-C_6)$alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)alkyl)_3$, $(C_2-C_6)$alkylcarbonylamino, $(C_2-C_6)$alkylaminocarbonyl, cyano, nitro, an aldehyde group and a radical of formula (II) with the condition that at least one carbon atom adjacent to the carbon atom of the $(C_5-C_{20})$heteroaryl substituted with the radical of formula (II) is substituted with hydrogen; or, alternatively, one, two or three of the pairs $R_1$ and $R_2$, $R_2$ and $R_3$, and $R_3$ and $R_4$, together with the carbon atoms to which they are attached, form a ring system comprising 1 to 5 rings, each ring being isolated, fused or partially fused, and comprising from 5 to 6 members selected from the group consisting of: C, CH, $CH_2$, CO, O, S, N and $NR_{10}$, wherein $R_{10}$ is selected from hydrogen and $(C_1-C_6)$alkyl, each ring being independently unsaturated, saturated or aromatic; and each ring being further optionally substituted with one or more radicals selected from the group consisting of: halogen, $(C_1-C_6)$alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)alkyl)_3$, $(C_2-C_6)$alkylcarbonylamino, $(C_2-C_6)$alkylaminocarbonyl, cyano, an aldehyde group and nitro and wherein when the ring system comprises at least one carbon-carbon double bond, the carbon atoms forming a double bond can further be substituted with a radical of formula (II) with the condition that the carbon atom forming the double bond adjacent to the carbon atom substituted with a radical of formula (II) is substituted with hydrogen;

$R_7$ is selected from the group consisting of hydrogen, $(C_1-C_6)$alkyl and $(C_1-C_6)$haloalkyl;

$R_8$ is selected from the group consisting of hydrogen, $(C_1-C_6)$alkyl, and $(C_1-C_6)$haloalkyl;

$R_9$ is a linear or branched $(C_1-C_6)$alkyl; and $R_{11}$, $R_{12}$, $R_{13}$, $R_{14}$ have the same meanings as $R_1$, $R_2$, $R_3$, $R_4$;

$R_5$ and $R_6$ are each independently selected from the group consisting of: hydrogen, straight chain or branched $(C_1-C_6)$alkyl, $(C_1-C_6)$haloalkyl, a $(C_6-C_{20})$aryl optionally substituted at one or more positions with a radical selected from the group consisting of halogen, $(C_1-C_6)$alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)alkyl)_3$, $(C_2-C_6)$alkylcarbonylamino, $(C_2-C_6)$alkylaminocarbonyl, cyano, nitro, an aldehyde group, and a radical of formula (II) with the condition that at least one carbon atom adjacent to the carbon atom of the $(C_6-C_{20})$aryl substituted with the radical of formula (II) is substituted with hydrogen; and a $(C_5-C_{20})$heteroaryl optionally substituted at one or more positions with a radical selected from the group consisting of: halogen, $(C_1-C_6)$alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)alkyl)_3$, $(C_2-C_6)$alkylcarbonylamino, $(C_2-C_6)$alkylaminocarbonyl, cyano, nitro, an aldehyde group, and a radical of formula (II) with the condition that at least one carbon atom adjacent to the carbon atom of the $(C_5-C_{20})$heteroaryl substituted with the radical of formula (II) is substituted with hydrogen; or, alternatively, $R_5$ and $R_6$, together with the carbon atoms to which they are attached, form a ring system comprising 1 to 10 rings, each ring being isolated, fused or partially fused, and comprising from 5 to 6 members selected from the group consisting of C, CH, $CH_2$, CO, O, S, N and $NR_{10}$, wherein $R_{10}$ is selected from hydrogen and $(C_1-C_6)$ alkyl, each ring being independently unsaturated, saturated or aromatic, and each ring being further optionally substituted with one or more radicals independently selected from the group consisting of: halogen, $(C_1-C_6)$alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)alkyl)_3$, $(C_2-C_6)$alkylcarbonylamino, $(C_2-C_6)$alkylaminocarbonyl, cyano, an aldehyde group, and nitro, and wherein when the ring system comprises at least one carbon-carbon double bond, the carbon atoms forming a double bond can further be substituted with a radical of formula (II) with the condition that the carbon atom forming the double bond adjacent to the carbon atom substituted with a radical of formula (II) is substituted with hydrogen;

to obtain a partially hydrogenated polyacene of formula (III):

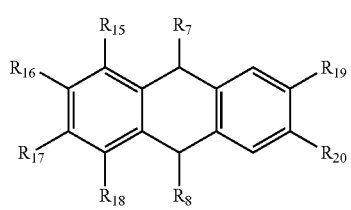

(III)

wherein the $R_{15}$, $R_{16}$, $R_{17}$, $R_{18}$, $R_{19}$, $R_{20}$ have the same meanings as $R_1$, $R_2$, $R_3$, $R_4$, $R_5$, $R_6$ respectively except when a radical of formula (II) is present in the compound of formula (I) then the diradical of formula (II') is cyclized in a diradical of formula (IV) in the compound of formula (III)

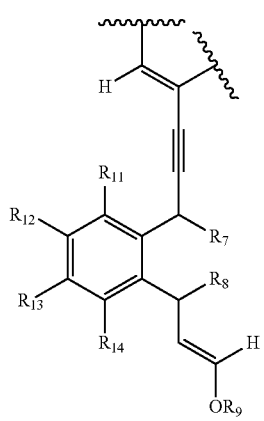

(II')

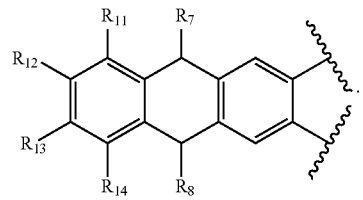

(IV)

2. The method according to claim 1 wherein each of $R_{11}$, $R_{12}$, $R_{13}$ and $R_{14}$, which may be the same or different, is independently selected from the group consisting of: hydrogen, halogen, straight chain or branched $(C_1-C_6)$alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)alkyl)_3$, $(C_2-C_6)$alkylcarbonylamino, $(C_2-C_6)$alkylaminocarbonyl, an aldehyde group, cyano, nitro, a $(C_6-C_{20})$aryl optionally substituted at one or more positions with a radical selected from the group consisting of halogen, $(C_1-C_6)$alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)alkyl)_3$, $(C_2-C_6)$alkylcarbonylamino, $(C_2-C_6)$alkylaminocarbonyl, cyano, nitro, and an aldehyde group and a $(C_5-C_{20})$heteroaryl optionally substituted at one or more positions with a radical selected from the group consisting of halogen, $(C_1-C_6)$alkyl, $(C_1-C_6)$haloalkyl, $(C_1-C_6)$alkyloxy, $(C_1-C_6)$thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)alkyl)_3$, $(C_2-C_6)$alkylcarbonylamino, $(C_2-C_6)$alkylaminocarbonyl, cyano, nitro, and an aldehyde group; or, alternatively, one, two or three of the pairs $R_{11}$ and $R_{12}$, $R_{12}$ and $R_{13}$, and $R_{13}$ and $R_{14}$, together with the carbon atoms to which they are attached, form a ring system comprising 1 to 5 rings, each ring being isolated, fused or partially fused, and comprising from 5 to 6 members selected from the group consisting of: C, CH, $CH_2$, CO, O, S, N and $NR_{10}$, wherein $R_{10}$ is selected from hydrogen and $(C_1-C_6)$alkyl, each ring being independently unsaturated, saturated or aromatic; and each ring being further optionally substituted with one or more radicals selected from the group consisting of: halogen, $(C_1-C_6)$alkyl, $(C_1-C_6)$haloalkyl, $(C_1-C_6)$alkyloxy, $(C_1-C_6)$ thioalkyl, $(C_2-C_6)$alkylcarbonyl, $(C_2-C_6)$alkylcarbonyloxy, $(C_2-C_6)$alkyloxycarbonyl, a radical of formula $Si((C_1-C_6)alkyl)_3$, $(C_2-C_6)$alkylcarbonylamino, $(C_2-C_6)$alkylaminocarbonyl, cyano, and aldehyde group, and nitro.

3. The method according to claim 2, wherein, in the compound of formula (I):

each of $R_1$, $R_2$, $R_3$ and $R_4$, which may be the same or different, are independently selected from the group consisting of: hydrogen, halogen, straight chain or branched $(C_1-C_6)$alkyl, $(C_1-C_6)$haloalkyl, $(C_1-C_6)$alkyloxy, $(C_1-C_6)$thioalkyl, $(C_1-C_6)$alkylcarbonyl, an aldehyde group, cyano, nitro; a $(C_6-C_{20})$aryl optionally substituted at one or more positions with a radical selected from the group consisting of halogen, $(C_1-C_6)$ alkyl, $(C_1-C_6)$haloalkyl, $(C_1-C_6)$alkyloxy, and $(C_1-C_6)$ thioalkyl; and a $(C_5-C_{20})$heteroaryl optionally substituted at one or more positions with a radical selected from the group consisting of halogen, $(C_1-C_6)$alkyl, $(C_1-C_6)$haloalkyl, $(C_1-C_6)$alkyloxy, and $(C_1-C_6)$thioalkyl; or, alternatively, one, two or three of the pairs $R_1$ and $R_2$, $R_2$ and $R_3$, and $R_3$ and $R_4$, together with the carbon atoms to which they are attached, form a ring system, said ring comprising 1 to 5 rings, each ring being isolated, fused or partially fused, and comprising from 5 to 6 members selected from the group consisting of C, CH, $CH_2$, O, and S, each ring being independently unsaturated, saturated or aromatic; and each ring being further optionally substituted with one or more radicals selected from the group consisting of: halogen, ($C_1$-$C_6$)alkyl, ($C_1$-$C_6$)haloalkyl, ($C_1$-$C_6$)alkyloxy, and nitro; and $R_5$ and $R_6$ are selected from the group consisting of hydrogen, straight chain or branched ($C_1$-$C_6$)alkyl, and a ($C_6$-$C_{20}$)aryl optionally substituted at one or more positions with a radical selected from the group consisting of halogen, ($C_1$-$C_6$)alkyl, and ($C_1$-$C_6$)haloalkyl; or, alternatively, $R_5$ and $R_6$, together with the carbon atoms to which they are attached, form a ring system comprising 1 to 5 aromatic rings, each ring being isolated, fused or partially fused, and comprising from 5 to 6 members selected from the group consisting of C, CH, CO, O, S, N and $NR_{10}$, wherein $R_{10}$ is selected from hydrogen and ($C_1$-$C_6$)alkyl and each ring being further optionally substituted with one or more radicals independently selected from the group consisting of halogen, ($C_1$-$C_6$) alkyl, ($C_1$-$C_6$)haloalkyl, ($C_1$-$C_6$)alkyloxy, ($C_1$-$C_6$)thioalkyl, ($C_2$-$C_6$)alkylcarbonyl, ($C_2$-$C_6$)alkylcarbonyloxy, ($C_2$-$C_6$)alkyloxycarbonyl, a radical of formula Si(($C_1$-$C_6$)alkyl)$_3$, ($C_2$-$C_6$)alkylcarbonylamino, ($C_2$-$C_6$)alkylaminocarbonyl, cyano, an aldehyde group, nitro, and a radical of formula (II) with the condition that the carbon atom of the ring system adjacent to the carbon atom substituted with a radical of formula (II) is substituted with hydrogen.

4. The method according to claim 3, wherein:

each of $R_1$, $R_2$, $R_3$ and $R_4$, which may be the same or different, are independently selected from the group consisting of: hydrogen, straight chain or branched ($C_1$-$C_6$)alkyl, and ($C_1$-$C_6$)haloalkyl; or, alternatively, one, two or three of the pairs $R_1$ and $R_2$, $R_2$ and $R_3$, and $R_3$ and $R_4$, together with the carbon atoms to which they are attached, form a ring system, said ring comprising 1 to 3 aromatic rings, each ring being isolated, or fused, and comprising 6 members selected from the group consisting of C and CH; and $R_5$ and $R_6$, together with the carbon atoms to which they are attached, form a ring system comprising 1 to 5 rings, each ring being isolated or fused, and comprising from 5 to 6 members selected from the group consisting of C, CH, and S, each ring being aromatic, and each ring being further optionally substituted with one or more radicals independently selected from the group consisting of halogen, ($C_1$-$C_6$)alkyl, ($C_1$-$C_6$)haloalkyl, ($C_1$-$C_6$)alkyloxy, ($C_1$-$C_6$)alkylcarbonyl, a radical of formula Si(($C_1$-$C_6$)alkyl)$_3$, an aldehyde group, and a radical of formula (II) with the condition that the carbon atom of the ring system adjacent to the carbon atom substituted with a radical of formula (II) is substituted with hydrogen.

5. The method according to claim 3, wherein each of $R_1$, $R_2$, $R_3$ and $R_4$ represent hydrogen; or, alternatively, one of the pairs selected from $R_1$ and $R_2$, and $R_2$ and $R_3$, together with the carbon atoms to which they are attached, form a phenyl ring; and $R_5$ and $R_6$, together with the carbon atoms to which they are attached, form a ring system selected from benzene, naphthalene, phenantrene, biphenyl, thiophene, benzothiophene and 5'-phenyl-1,1':3',1"-terphenyl, wherein said ring system is further optionally substituted with one or more radicals independently selected from the group consisting of bromo, fluoro, iodo, methyl, methoxy, trimethylsilyl, acetyl, an aldehyde group, and a radical selected from the group consisting of the radicals of formula (IIa), (IIb) and (IIc)

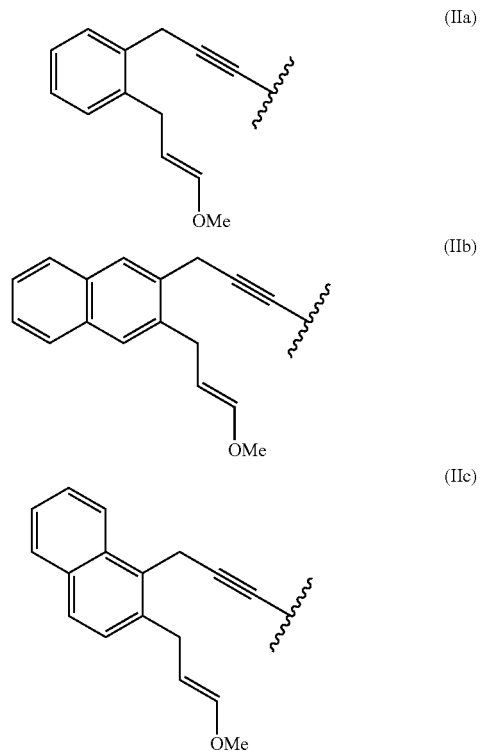

with the condition that the carbon atom of the ring system adjacent to the carbon atom substituted with a radical of formula (IIa), or alternatively (IIb), or alternatively (IIc) is substituted with hydrogen.

6. The method according to claim 5, wherein:

$R_7$ is hydrogen;

$R_8$ is hydrogen; and $R_9$ is methyl.

7. The method according to claim 1, wherein the Au(I) catalyst is a Au(I) complex with one or more ligands wherein the ligand is selected from the group consisting of phosphines, phosphites and N-heterocyclic carbenes.

8. The method according to claim 7, wherein the Au(I) catalyst is selected from the catalysts of formula (A), (B) and (C):

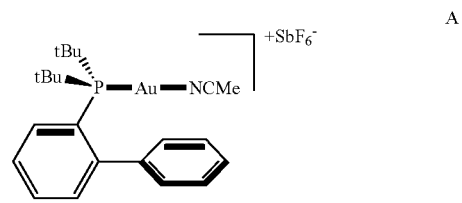

-continued

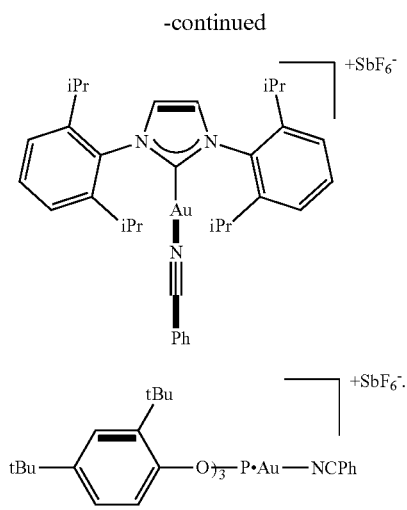

9. The method according to claim 1, further comprising the previous step of producing the compound of formula (I) by reacting the compound of formula (V)

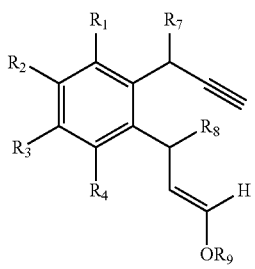

with a compound of formula X—CR$_5$=CHR$_6$ in the presence of a catalyst and a ligand; wherein R$_1$ to R$_9$ are as defined in claim 1 and X is a leaving group.

10. The method according to claim 9, further comprising the previous step of producing the compound of formula (V) by reacting the compound of formula (VI)

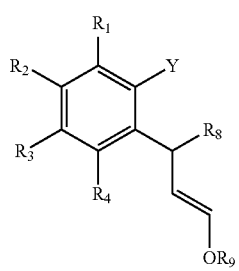

with a compound of formula H$_3$COR$_7$=C=CH$_2$ wherein Y is halogen and wherein R$_1$ to R$_9$ are as defined in claim 9.

11. The method according to claim 10, wherein the compound of formula (III) is selected from the group consisting of 5,12 dihydrotetracene; 8,13 dihydrobenzo[a]tetracene; 10,15-dihydrodibenzo[a,c]tetracene, 7-methyl-5,12-dihydrotetracene, 8-methyl-5,12-dihydrotetracene; 7,9 dimethyl-5,12-dihydrotetracene; 7-methoxy-5,12-dihydrotetracene; 8-methoxy-5,12-dihydrotetracene; 1-(6,11-dihydrotetracen-2-yl)ethan-1-one, 6,11-dihydrotetracen-2-carbaldehyde; 8-fluoro-5,12 dihydrotetracene; 8-bromo-5,12 dihydrotetracene; 8-iodo-5,12 dihydrotetracene; 6,11 dihydrotetracene-2-yl)trimethylsilane; 7-phenyl-5,12 dihydrotetracene; 8-(4-iodophenyl) 5,12 dihydrotetracene; 5,10-dihydroanthra[2,3-b]thiophene; 7,12-dihydroanthra[2,3-b]benzo[d]thiophene; 7,16-dihydrodibenzo[a,j]tetracene; 6,13 dihydropentacene; 6,6',11,11'-tetrahydro-2,2'-bitetracene; 5,9,14,18 tetrahydroheptacene; 1,3,5-tris(6,11-dihydrotetracen-2-yl)benzene; 7,11,18,22-tetrahydrodibenzol[a,p]heptacene, and 6,10,17,21-tetrahydrononacene.

12. A method for the preparation of a polyacene compound comprising the steps of claim 10, and further comprising a final step of oxidizing the compound of formula (III) to form a compound of formula (VII):

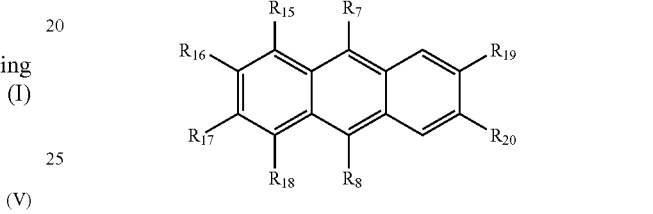

wherein R$_7$, R$_8$, R$_{15}$, R$_{16}$, R$_{17}$, R$_{18}$, R$_{19}$ and R$_{20}$ are as defined in claim 1, except the diradical of formula (IV) in the compound of formula (III), which is replaced by a diradical of formula (VIII) in the compound of formula (VII):0

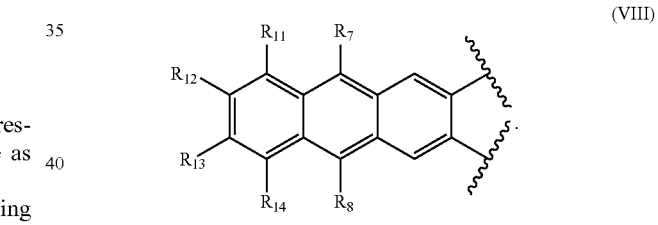

13. A compound of formula (I'):

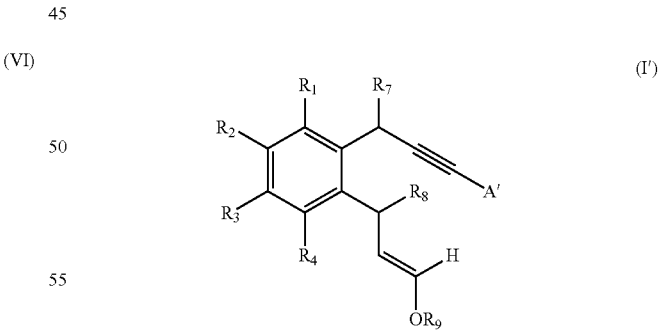

wherein A' is selected from hydrogen and a radical of formula —CR$_5$=CHR$_6$ wherein R$_1$ to R$_9$ are as defined in claim 1.

14. The compound of formula (I') according to claim 13 that is selected from the group consisting of 1-(3-methoxyallyl)-2-(prop-2-yn-1-yl)benzene; 2-(3-methoxyallyl)-3-(prop-2-yn-1-yl) naphthalene; 2-(3-methoxyallyl)-1-(prop-2-yn-1-yl)naphthalene; 1-(3-Methoxyallyl)-2-(3-phenylprop-2-yn-1-yl)benzene; 2-(3-(2-(3-Methoxyallyl)

phenyl)prop-1-yn-1-yl)naphthalene; 9-(3-(2-(3-Methoxyallyl)phenyl)prop-1-yn-1-yl)phenanthrene; 1-(3-Methoxyallyl)-2-(3-(o-tolyl)prop-2-yn-1-yl)benzene; 1-(3-Methoxyallyl)-2-(3-(p-tolyl)prop-2-yn-1-yl)benzene; 1-(3-(2-(3-Methoxyallyl)phenyl)prop-1-yn-1-yl)-3,5-dimethylbenzene; 1-Methoxy-2-(3-(2-(3-methoxyallyl)phenyl)prop-1-yn-1-yl)benzene; 1-(3-Methoxyallyl)-2-(3-(4-methoxyphenyl)prop-2-yn-1-yl)benzene; 1-(4-(3-(2-(3-Methoxyallyl)phenyl)prop-1-yn-1-yl)phenyl)ethan-1-one 4-(3-(2-(3-Methoxyallyl)phenyl)prop-1-yn-1-yl)benzaldehyde; 1-(3-(4-Fluorophenyl)prop-2-yn-1-yl)-2-(3-methoxyallyl)benzene; 1-(3-(4-Bromophenyl)prop-2-yn-1-yl)-2-(3-methoxyallyl)benzene; 1-(3-(4-Iodophenyl)prop-2-yn-1-yl)-2-(3-methoxyallyl)benzene; (4-(3-(2-(3-Methoxyallyl)phenyl)prop-1-yn-1-yl)phenyl)trimethyl silane; 2-(3-(2-(3-Methoxyallyl)phenyl)prop-1-yn-1-yl)-1,1'-biphenyl; 4-Iodo-4'-(3-(2-(3-methoxyallyl)phenyl)prop-1-yn-1-yl)-1,1'-biphenyl; 2-(3-(2-(3-Methoxyallyl)phenyl)prop-1-yn-1-yl)thiophene; 2-(3-(2-(3-Methoxyallyl)phenyl)prop-1-yn-1-yl)benzo[b]thiophene; 2-(3-Methoxyallyl)-1-(3-(naphthalen-2-yl)prop-2-yn-1-yl)naphthalene; 2-(3-Methoxyallyl)-3-(3-phenylprop-2-yn-1-yl)naphthalene; 4,4'-Bis(3-(2-(3-methoxyallyl)phenyl)prop-1-yn-1-yl)-1,1'-biphenyl; (2,5-Bis(3-(2-(3-methoxyallyl)phenyl)prop-1-yn-1-yl)-1,4-phenylene)bis(trimethylsilane); 4,4''-Bis(3-(2-(3-methoxyallyl)phenyl)prop-1-yn-1-yl)-5'-(4-(3-(2-(3-methoxyallyl)phenyl)prop-1-yn-1-yl)phenyl)-1,1':3',1''-terphenyl; 1,4-Bis(3-(2-(3-methoxyallyl)naphthalen-1-yl)prop-1-yn-1-yl)benzene; and 1,4-Bis(3-(3-(3-methoxyallyl)naphthalen-2-yl)prop-1-yn-1-yl)benzene.

15. The compound of claim 13, wherein A' is selected from the group consisting of hydrogen and a radical of formula —CR$_5$=CHR$_6$, wherein:
  each of R$_1$, R$_2$, R$_3$ and R$_4$, which may be the same or different, are independently selected from the group consisting of: hydrogen, halogen, straight chain or branched (C$_1$-C$_6$)alkyl, (C$_1$-C$_6$)haloalkyl, (C$_1$-C$_6$)alkyloxy, (C$_1$-C$_6$)thioalkyl, (C$_1$-C$_6$)alkylcarbonyl, an aldehyde group, cyano, nitro; a (C$_6$-C$_{20}$)aryl optionally substituted at one or more positions with a radical selected from the group consisting of halogen, (C$_1$-C$_6$) alkyl, (C$_1$-C$_6$)haloalkyl, (C$_1$-C$_6$)alkyloxy, and (C$_1$-C$_6$) thioalkyl; and a (C$_5$-C$_{20}$)heteroaryl optionally substituted at one or more positions with a radical selected from the group consisting of halogen, (C$_1$-C$_6$)alkyl, (C$_1$-C$_6$)haloalkyl, (C$_1$-C$_6$)alkyloxy, and (C$_1$-C$_6$)thioalkyl; or, alternatively,
  one, two or three of the pairs R$_1$ and R$_2$, R$_2$ and R$_3$, and R$_3$ and R$_4$, together with the carbon atoms to which they are attached, form a ring system, said ring comprising 1 to 5 rings, each ring being isolated, fused or partially fused, and comprising from 5 to 6 members selected from the group consisting of C, CH, CH$_2$, O, and S, each ring being independently unsaturated, saturated or aromatic; and each ring being further optionally substituted with one or more radicals selected from the group consisting of: halogen, (C$_1$-C$_6$)alkyl, (C$_1$-C$_6$)haloalkyl, (C$_1$-C$_6$)alkyloxy, and nitro;
  R$_7$ is selected from the group consisting of hydrogen, (C$_1$-C$_6$)alkyl and (C$_1$-C$_6$)haloalkyl;
  R$_8$ is selected from the group consisting of hydrogen, (C$_1$-C$_6$)alkyl, and (C$_1$-C$_6$)haloalkyl;
  R$_9$ is a linear or branched (C$_1$-C$_6$)alkyl; and
  R$_5$ and R$_6$ are selected from the group consisting of hydrogen, straight chain or branched (C$_1$-C$_6$)alkyl, and a (C$_6$-C$_{20}$)aryl optionally substituted at one or more positions with a radical selected from the group consisting of halogen, (C$_1$-C$_6$)alkyl, and (C$_1$-C$_6$)haloalkyl; or, alternatively,
  R$_5$ and R$_6$, together with the carbon atoms to which they are attached, form a ring system comprising 1 to 5 aromatic rings, each ring being isolated, fused or partially fused, and comprising from 5 to 6 members selected from the group consisting of C, CH, CO, O, S, N and NR$_{10}$, wherein R$_{10}$ is selected from hydrogen and (C$_1$-C$_6$)alkyl and each ring being further optionally substituted with one or more radicals independently selected from the group consisting of halogen, (C$_1$-C$_6$) alkyl, (C$_1$-C$_6$)haloalkyl, (C$_1$-C$_6$)alkyloxy, (C$_1$-C$_6$)thioalkyl, (C$_2$-C$_6$)alkylcarbonyl, (C$_2$-C$_6$)alkylcarbonyloxy, (C$_2$-C$_6$)alkyloxycarbonyl, a radical of formula Si((C$_1$-C$_6$)alkyl)$_3$, (C$_2$-C$_6$)alkylcarbonylamino, (C$_2$-C$_6$)alkylaminocarbonyl, cyano, an aldehyde group, nitro, and a radical of formula (II) with the condition that the carbon atom of the ring system adjacent to the carbon atom substituted with a radical of formula (II) is substituted with hydrogen.

16. The compound of claim 15, wherein A' is selected from the group consisting of hydrogen and a radical of formula —CR$_5$=CHR$_6$, wherein:
  each of R$_1$, R$_2$, R$_3$ and R$_4$, which may be the same or different, are independently selected from the group consisting of: hydrogen, straight chain or branched (C$_1$-C$_6$)alkyl, and (C$_1$-C$_6$)haloalkyl; or, alternatively,
  one, two or three of the pairs R$_1$ and R$_2$, R$_2$ and R$_3$, and R$_3$ and R$_4$, together with the carbon atoms to which they are attached, form a ring system, said ring comprising 1 to 3 aromatic rings, each ring being isolated, or fused, and comprising 6 members selected from the group consisting of C and CH; and
  R$_5$ and R$_6$, together with the carbon atoms to which they are attached, form a ring system comprising 1 to 5 rings, each ring being isolated or fused, and comprising from 5 to 6 members selected from the group consisting of C, CH, and S, each ring being aromatic, and each ring being further optionally substituted with one or more radicals independently selected from the group consisting of halogen, (C$_1$-C$_6$)alkyl, (C$_1$-C$_6$)haloalkyl, (C$_1$-C$_6$)alkyloxy, (C$_1$-C$_6$)alkylcarbonyl, a radical of formula Si((C$_1$-C$_6$)alkyl)$_3$, an aldehyde group, and a radical of formula (II) with the condition that the carbon atom of the ring system adjacent to the carbon atom substituted with a radical of formula (II) is substituted with hydrogen.

17. The compound of claim 16, wherein A' is selected from the group consisting of hydrogen and a radical of formula —CR$_5$=CHR$_6$, wherein:
  each of R$_1$, R$_2$, R$_3$ and R$_4$ represent hydrogen; or, alternatively, one of the pairs selected from R$_1$ and R$_2$, and R$_2$ and R$_3$, together with the carbon atoms to which they are attached, form a phenyl ring; and
  R$_5$ and R$_6$, together with the carbon atoms to which they are attached, form a ring system selected from benzene, naphthalene, phenantrene, biphenyl, thiophene, benzothiophene and 5'-phenyl-1,1':3',1''-terphenyl, wherein said ring system is further optionally substituted with one or more radicals independently selected from the group consisting of bromo, fluoro, iodo, methyl, methoxy, trimethylsilyl, acetyl, an aldehyde group, and a radical selected from the group consisting of the radicals of formula (IIa), (IIb) and (IIc)

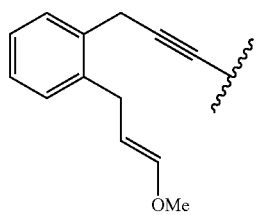
(IIa)

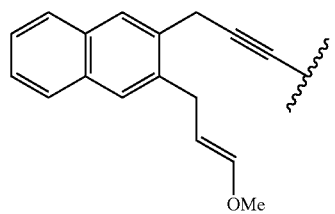
(IIb)

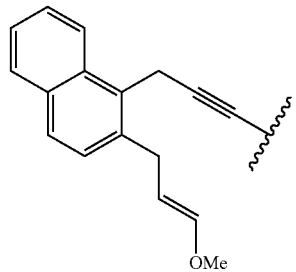
(IIc)

with the condition that the carbon atom of the ring system adjacent to the carbon atom substituted with a radical of formula (IIa), or alternatively (IIb), or alternatively (IIc) is substituted with hydrogen.

18. The compound of claim 17, wherein A' is selected from the group consisting of hydrogen and a radical of formula —CR$_5$═CHR$_6$, wherein:
R$_7$ is hydrogen;
R$_8$ is hydrogen; and
R$_9$ is methyl.

* * * * *